(12) United States Patent
Zhao et al.

(10) Patent No.: US 11,284,952 B2
(45) Date of Patent: **\*Mar. 29, 2022**

(54) ESTIMATION OF A POSITION AND ORIENTATION OF A FRAME USED IN CONTROLLING MOVEMENT OF A TOOL

(71) Applicant: Intuitive Surgical Operations, Inc., Sunnyvale, CA (US)

(72) Inventors: Tao Zhao, Sunnyvale, CA (US); Giuseppe Maria Prisco, Mountain View, CA (US); John R. Steger, Sunnyvale, CA (US); David Q. Larkin, Menlo Park, CA (US)

(73) Assignee: Intuitive Surgical Operations, Inc., Sunnyvale, CA (US)

( \* ) Notice: Subject to any disclaimer, the term of this patent is extended or adjusted under 35 U.S.C. 154(b) by 93 days.

This patent is subject to a terminal disclaimer.

(21) Appl. No.: 16/779,564

(22) Filed: Jan. 31, 2020

(65) Prior Publication Data
US 2020/0170725 A1    Jun. 4, 2020

Related U.S. Application Data

(63) Continuation of application No. 15/719,275, filed on Sep. 28, 2017, now Pat. No. 10,582,974, which is a
(Continued)

(51) Int. Cl.
*A61B 34/30* (2016.01)
*B25J 9/16* (2006.01)
(Continued)

(52) U.S. Cl.
CPC ............ *A61B 34/30* (2016.02); *A61B 34/37* (2016.02); *A61B 90/361* (2016.02);
(Continued)

(58) Field of Classification Search
CPC . A61B 2019/5255; A61B 34/30; A61B 34/37; A61B 90/361; A61B 34/35;
(Continued)

(56) References Cited

U.S. PATENT DOCUMENTS

| 5,053,975 A | 10/1991 | Tsuchihashi et al. |
| 5,631,973 A | 5/1997 | Green |

(Continued)

FOREIGN PATENT DOCUMENTS

| EP | 2277441 A1 | 1/2011 |
| JP | H07504363 A | 5/1995 |

(Continued)

OTHER PUBLICATIONS

Advisory Action dated May 26, 2015 for U.S. Appl. No. 13/360,380, filed Jan. 27, 2012, 3 pages (ISRG02510/US).
(Continued)

*Primary Examiner* — Ryan Rink
(74) *Attorney, Agent, or Firm* — Ferguson Braswell Fraser Kubasta PC

(57) ABSTRACT

A system includes a control device, a manipulator configured to support a tool having a tool frame, and at least one processor coupled to the control device and the manipulator. The at least one processor is configured to perform a method. The method includes receiving one or more images captured by an image-capturing system, the image-capturing system having an image frame. The tool is visible in the one or more images. The method further includes determining, based on information in the one or more images, an estimated frame transform relating the image frame and the tool frame, determining, based on the estimated frame transform, an output movement for the tool in response to an input at the control device, and causing movement of the tool according to the output movement.

20 Claims, 13 Drawing Sheets

Related U.S. Application Data continuation of application No. 14/997,257, filed on Jan. 15, 2016, now Pat. No. 9,827,057, which is a continuation of application No. 13/360,380, filed on Jan. 27, 2012, now Pat. No. 9,259,289.

(60) Provisional application No. 61/485,706, filed on May 13, 2011.

(51) Int. Cl.
*A61B 90/00* (2016.01)
*A61B 34/37* (2016.01)
*A61B 34/20* (2016.01)

(52) U.S. Cl.
CPC .......... *B25J 9/1689* (2013.01); *B25J 9/1697* (2013.01); *A61B 2034/2065* (2016.02)

(58) Field of Classification Search
CPC ............ A61B 34/70; A61B 2034/2055; A61B 2090/364; B25J 9/1689; B25J 9/1697; B25J 19/023; G05B 2219/45117; G05B 2219/39389; G05B 2219/45118; G05B 2219/39016; G05B 2219/39057; G05B 2219/40543; G05B 2219/40557
See application file for complete search history.

(56) References Cited

U.S. PATENT DOCUMENTS

| | | | |
|---|---|---|---|
| 5,859,934 A | 1/1999 | Green | |
| 6,236,896 B1 | 5/2001 | Watanabe et al. | |
| 6,394,998 B1 | 5/2002 | Wallace et al. | |
| 6,424,885 B1 * | 7/2002 | Niemeyer ............ | A61B 34/70 600/109 |
| 6,493,608 B1 | 12/2002 | Niemeyer et al. | |
| 6,799,065 B1 | 9/2004 | Niemeyer | |
| 6,936,042 B2 | 8/2005 | Wallace et al. | |
| 7,736,356 B2 | 6/2010 | Cooper et al. | |
| 7,780,651 B2 | 8/2010 | Madhani et al. | |
| 8,000,890 B2 | 8/2011 | Litvin et al. | |
| 8,419,717 B2 | 4/2013 | Diolaiti et al. | |
| 8,971,597 B2 | 3/2015 | Zhao et al. | |
| 9,259,289 B2 | 2/2016 | Zhao et al. | |
| 9,827,057 B2 | 11/2017 | Zhao et al. | |
| 10,582,974 B2 | 3/2020 | Zhao et al. | |
| 2005/0027397 A1 | 2/2005 | Niemeyer | |
| 2006/0258938 A1 | 11/2006 | Hoffman et al. | |
| 2009/0033655 A1 | 2/2009 | Boca et al. | |
| 2009/0088897 A1 | 4/2009 | Zhao et al. | |
| 2009/0326556 A1 | 12/2009 | Diolaiti et al. | |
| 2010/0168562 A1 | 7/2010 | Zhao et al. | |
| 2010/0168763 A1 | 7/2010 | Zhao et al. | |
| 2011/0071543 A1 | 3/2011 | Prisco et al. | |
| 2011/0113852 A1 | 5/2011 | Prisco | |
| 2011/0201885 A1 | 8/2011 | Okamura et al. | |
| 2012/0290134 A1 * | 11/2012 | Zhao ...................... | B25J 9/1689 700/259 |
| 2013/0063580 A1 | 3/2013 | Ogawa et al. | |
| 2013/0226197 A1 | 8/2013 | Diolaiti et al. | |
| 2018/0014895 A1 | 1/2018 | Zhao et al. | |

FOREIGN PATENT DOCUMENTS

| | | |
|---|---|---|
| JP | H07311610 A | 11/1995 |
| JP | H09128549 A | 5/1997 |
| JP | H1097311 A | 4/1998 |
| JP | H1190868 A | 4/1999 |
| WO | WO-2006124388 A1 | 11/2006 |
| WO | WO-2010048160 A2 | 4/2010 |
| WO | WO-2010048164 A2 | 4/2010 |
| WO | WO-2012158458 A2 | 11/2012 |

OTHER PUBLICATIONS

Craig, John J., "Introduction to Robotics Mechanics and Control," 2nd Edition, Addison-Wesley Publishing Company, Inc., 1986; Chap. 2, "Spatial Descriptions and Transformations", pp. 15-59.
Extended European Search Report for Application No. 20120785315, dated Jan. 29, 2015, 6 pages (ISRG02510/EP).
Extended European Search Report for Application No. EP18179651.7, dated Sep. 25, 2018, 6 pages (ISRG02510D1/EP).
Final Office Action dated Jun. 3, 2014 for U.S. Appl. No. 13/360,380, filed Jan. 27, 2012, 13 pages (ISRG02510/US).
Final Office Action dated Mar. 17, 2015 for U.S. Appl. No. 13/360,380, filed Jan. 27, 2012, 12 pages (ISRG02510/US).
International Preliminary Report on Patentability for Application No. PCT/US2012/037310, dated Nov. 28, 2013, 6 pages (ISRG02510/PCT).
International Search Report and Written Opinion for Application No. PCT/US2012/037310, dated Nov. 14, 2012, 10 pages.
Non-Final Office Action dated Feb. 11, 2014 for U.S. Appl. No. 13/360,380, filed Jan. 27, 2012, 12 pages (ISRG02510/US).
Non-Final Office Action dated Oct. 30, 2014 for U.S. Appl. No. 13/360,380, filed Jan. 27, 2012, 12 pages (ISRG02510/US).
Notice of Allowance dated Jul. 6, 2017 for U.S. Appl. No. 14/997,257, filed Jan. 15, 2016, 5 pages (ISRG02510C1/US).
Notice of Allowance dated Oct. 6, 2015 for U.S. Appl. No. 13/360,380, filed Jan. 27, 2012, 5 pages (ISRG02510/US).
Office Action dated Jul. 2, 2015 for Chinese Application No. 201280023715.8 filed May 10, 2012, 32 pages (ISRG02510/CN).
Office Action dated Jan. 5, 2016 for Japanese Application No. 20140510464 filed May 10, 2012, 8 pages (ISRG02510/JP).
Office Action dated Jan. 7, 2014 for European Application No. 12785315.8 filed May 10, 2012, 3 pages (ISRG02510/EP).
Office Action dated Feb. 17, 2015 for European Application No. 12785315.8 filed May 10, 2012, 1 page (ISRG02510/EP).
Response filed May 9, 2014 to Non-Final Office Action dated Feb. 11, 2014 for U.S. Appl. No. 13/360,380, filed Jan. 27, 2012, 14 pages (ISRG02510/US).
Response filed Jul. 17, 2015 to Final Office Action dated Mar. 17, 2015 for U.S. Appl. No. 13/360,380, filed Jan. 27, 2012, 13 pages (ISRG02510/US).
Response filed May 18, 2015 to Final Office Action dated Mar. 17, 2015 for U.S. Appl. No. 13/360,380, filed Jan. 27, 2012, 20 pages (ISRG02510/US).
Response filed Aug. 22, 2014 to Final Office Action dated Jun. 3, 2014 for U.S. Appl. No. 13/360,380, filed Jan. 27, 2012, 13 pages (ISRG02510/US).
Response filed Jan. 30, 2015 to Non-Final Office Action dated Oct. 30, 2014 for U.S. Appl. No. 13/360,380, filed Jan. 27, 2012, 17 pages (ISRG02510/US).
Shiu Y. C., et al., "Pose Determination of Cylinders, Cones, and Spheres from Perspective Projections," Applications of Artificial Intelligence X: Machine Vision and Robotics, 1992, SPIE, vol. 1708, pp. 771-782.
Vertut, Jean and Phillips Coiffet, Robot Technology: Teleoperation and Robotics Evolution and Development, English translation, Prentice-Hall, Inc., Inglewood Cliffs, NJ, USA 1986, vol. 3A, 332 pages.
Non-Final Office Action dated May 1, 2019 for U.S. Appl. No. 15/719,275, filed Sep. 28, 2017, 13 pages (ISRG02510C2/US).

* cited by examiner

ESTIMATION OF A POSITION AND ORIENTATION OF A FRAME USED IN CONTROLLING MOVEMENT OF A TOOL

CROSS-REFERENCE TO RELATED APPLICATIONS

This application is a continuation of and claims the benefit of priority under 35 U.S.C. § 120 to U.S. patent application Ser. No. 15/719,275, filed on Sep. 28, 2017, which is a continuation of and claims the benefit of priority under 35 U.S.C. § 120 to U.S. patent application Ser. No. 14/997,257, filed on Jan. 15, 2016, which is a continuation of and claims the benefit of priority under 35 U.S.C. § 120 to U.S. patent application Ser. No. 13/360,380, filed on Jan. 27, 2012, which claims the benefit of priority under 35 U S.C. § 119(e) to U.S. Provisional Patent Application Ser. No. 61/485,706, filed on May 13, 2011, each of which is hereby incorporated by reference herein in its entirety.

BACKGROUND

The present invention generally relates to robotic systems and in particular, to estimation of a position and orientation of a frame used in controlling operator commanded movement of a tool.

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using such medical robotic systems is strong and growing.

Examples of medical robotic systems include the daVinci® Surgical System, the daVinci S® Surgical System, and the daVinci® Si HD™ Surgical System from Intuitive Surgical, Inc., of Sunnyvale, Calif. Each of these systems includes a surgeon's workstation, a patient-side cart, a high performance three-dimensional ("3-D") vision system, and Intuitive Surgical's proprietary EndoWrist® articulating instruments, which are modeled after the human wrist so that when added to the motions of the slave manipulator holding the surgical instrument, they allow at least a full six degrees of freedom of motion, which is comparable to or even greater than the natural motions of open surgery.

The daVinci® surgeon's workstation has a high-resolution stereoscopic video display. The system offers higher fidelity than polarization, shutter eyeglass, or other 3-D display techniques. Each eye views a separate display that presents the left or right eye perspective through an objective lens and a series of mirrors. The surgeon sits comfortably and looks into this display throughout surgery, making it an ideal place for the surgeon to display and manipulate 3-D intraoperative imagery.

The patient-side cart typically includes three or more slave manipulators for holding and manipulating medical devices such as surgical instruments and image capturing devices for performing and viewing a medical procedure at a surgical site within a patient. To manipulate these medical devices, the surgeon's workstation also includes master control devices which may be selectively associated with the medical devices (and the slave manipulators holding the medical devices) to manipulate them.

In such a medical robotic system, as well as other robotic systems in general, the control of a surgical instrument in response to operator manipulation of a master control device may have a number of definable reference frames and corresponding frame transforms to map points in one frame to corresponding points in another frame. When the position and orientation of one of the frames is unknown, however, precise control of the surgical instrument may be difficult to achieve so that the safety of a patient being treated at the time by the medical robotic system as well as the successful completion of a procedure being performed on the patient may be jeopardized.

SUMMARY

In general in one aspect, one or more embodiments relate to a system comprising a control device; a manipulator configured to support a tool having a tool frame; and at least one processor coupled to the control device and the manipulator, the at least one processor configured to perform a method comprising: receiving one or more images captured by an image-capturing system, the image-capturing system having an image frame, wherein the tool is visible in the one or more images; determining, based on information in the one or more images, an estimated frame transform relating the image frame and the tool frame; determining, based on the estimated frame transform, an output movement for the tool in response to an input at the control device; and causing movement of the tool according to the output movement.

In general, in one aspect, one or more embodiments relate to a method for operating a system comprising a control device and a manipulator configured to support a tool having a tool frame, the method comprising: receiving one or more images captured by an image-capturing system, the image-capturing system having an image frame, wherein the tool is visible in the one or more images; determining, based on information in the one or more images, an estimated frame transform relating the image frame and the tool frame; determining, based on the estimated frame transform, an output movement for the tool in response to an input at the control device; and causing movement of the tool according to the output movement.

In general, in one aspect, one or more embodiments relate to a non-transitory machine-readable medium comprising a plurality of machine-readable instructions executed by one or more processors associated with a system, the system comprising a control device and a manipulator configured to support a tool having a tool frame, and the plurality of machine-readable instructions causing the one or more processors to perform a method comprising: receiving one or more images captured by an image-capturing system, the image-capturing system having an image frame, wherein the tool is visible in the one or more images; determining, based on information in the one or more images, an estimated frame transform relating the image frame and the tool frame; determining, based on the estimated frame transform, an output movement for the tool in response to an input at the control device; and causing movement of the tool according to the output movement.

Other aspects of the invention will be apparent from the following description and the appended claims.

DETAILED DESCRIPTION

Figure 1:
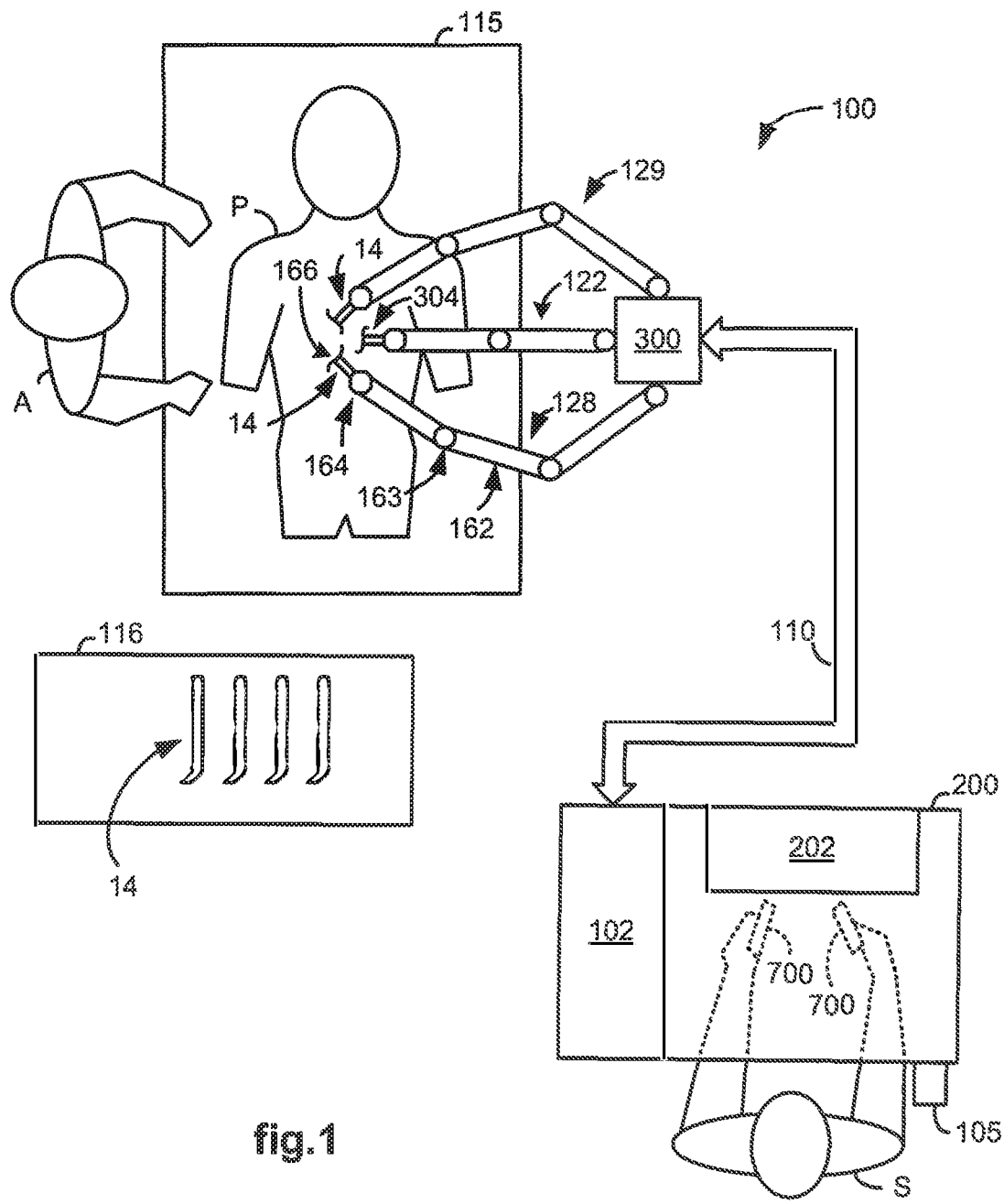
FIG. 1 illustrates a top view of an operating room employing a medical robotic system utilizing aspects of the present invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Although the following example describes application of the present invention to a medical robotic system, it is to be appreciated that the present invention is not to be so limited. In particular, the present invention is applicable to robotic systems in general and should be accorded its full scope according to the attached claims.

FIG. 1 illustrates, as an example, a top view of an operating room employing a medical robotic system 100. The medical robotic system in this case is a minimally invasive robotic surgical system including a workstation 200 utilized by a surgeon ("S") while performing a medical procedure, such as a diagnostic or surgical procedure, with assistance from one or more assistants ("A"), on a patient ("P") who is lying face up on an operating table 115.

The workstation 200 includes a 3-D display 202 for displaying a 3-D image of a surgical or work site to the surgeon, left and right master control devices 700, 700, a foot pedal 105, and a processor 102. The control devices 700, 700 may include any one or more of a variety of input devices such as joysticks, gloves, trigger-guns, hand-operated controllers, or the like. In the present example, they are implemented as pinchers that may be opened and closed and moved in multiple degrees of freedom to correspond to desired movement of their respectively associated surgical tools. The processor 102 may be a dedicated computer integrated into the workstation 200 or positioned next or near to it, or the processor 102 may be broken up into a number of processing or controller components that are distributed in a distributed processing fashion throughout the system 100.

The surgeon performs a medical procedure by manipulating the master control devices 700, 700 (also referred to as "master manipulators") so that the processor 102 causes slave manipulators of their respectively associated robotic arm assemblies 128, 129 to manipulate their respective removably coupled tools 14, 14 (also referred to as "surgical instruments") accordingly, while the surgeon views the surgical site in 3-D on the workstation 200 display 202 as it is captured by an image capturing device, which in the present example, is a stereoscopic endoscope 304 having a pair of cameras which capture corresponding images for stereo vision.

Each of the tools 14, 14, as well as the endoscope 304, is conventionally inserted in this example through a tool guide into the patient so as to extend down to the surgical site through a corresponding minimally invasive incision such as incision 166. The number of surgical tools used at one time and consequently, the number of robotic arms being used in the system 100 will generally depend on the medical procedure being performed and the space constraints within the operating room, among other factors. If it is necessary to change a tool being used during a procedure, the assistant may remove the tool no longer being used from its robotic arm assembly, and replace it with another tool 14 from a tray 116 in the operating room.

So that the tools 14, 14 may be manipulated at the surgical site, they each have a wrist mechanism including joints (or other drivable mechanical elements such as gears, spools, etc.) for controlling the orientation of the wrist mechanism, and an additional joint (or other drivable mechanical element) controlling the eventual grip or other end effector joint of the tool. For additional details on such a tool wrist and end effector mechanism (and the mechanical elements and other linkages driving them), see, e.g., U.S. Pat. No. 7,780,651 (filed Nov. 27, 2007; entitled "Articulated Surgical Instrument for Performing Minimally Invasive Surgery with Enhanced Dexterity and Sensitivity"), U.S. Pat. No. 6,936,902 (filed Apr. 16, 2002; entitled "Surgical Tools for Use in Minimally Invasive Telesurgical Applications"), and U.S. Pat. No. 7,736,356 (filed Nov. 1, 2004; entitled "Surgical Tool Having Positively Positionable Tendon-Actuated Multi-Disk Wrist Joint"), which are incorporated herein by reference.

Each of the robotic arm assemblies 122, 128, 129 includes a slave arm (also referred to as a "slave manipulator") and a setup arm. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arm assemblies 122, 128, 129 so that their respective medical devices may be inserted into their respective tool guides. Alternatively, the setup arms may be actively controlled using motor controlled joints.

The display 202 is positioned near the surgeon's hands so that it will display a projected image that is oriented so that the surgeon feels that he or she is actually looking directly down onto the operating site. To that end, images of the tools 14, 14 appear to be located substantially where the surgeon's hands are located to give a sense of telepresence to the surgeon (e.g., the perception that the master control devices are integral with the surgical tools).

The processor 102 performs various functions in the system 100. One important function that it performs is to translate and transfer the mechanical motion of control devices 700, 700 to their respective slave manipulators of robotic arm assemblies 128, 129 through control signals over bus 110 so that the surgeon can effectively manipulate their respective tools 14, 14. Another important function is to implement various control system processes and methods as described herein.

Although described as a processor, it is to be appreciated that the processor 102 may be implemented in practice by any combination of hardware, software, and firmware. Also, the processor functions as described herein may be performed by one unit or divided up among different components, each of which may be implemented in turn by any combination of hardware, software and firmware.

For additional details on the construction and operation of medical robotic systems such as described herein, see, e.g., U.S. Pat. No. 6,493,608 (filed Apr. 7, 1999; entitled "Aspects of a Control System of a Minimally Invasive Surgical Apparatus") and U.S. Pat. No. 6,424,885 (filed Aug. 13, 1999; entitled "Camera Referenced Control in a Minimally Invasive Surgical Apparatus"), which are incorporated herein by reference.

Figure 2:
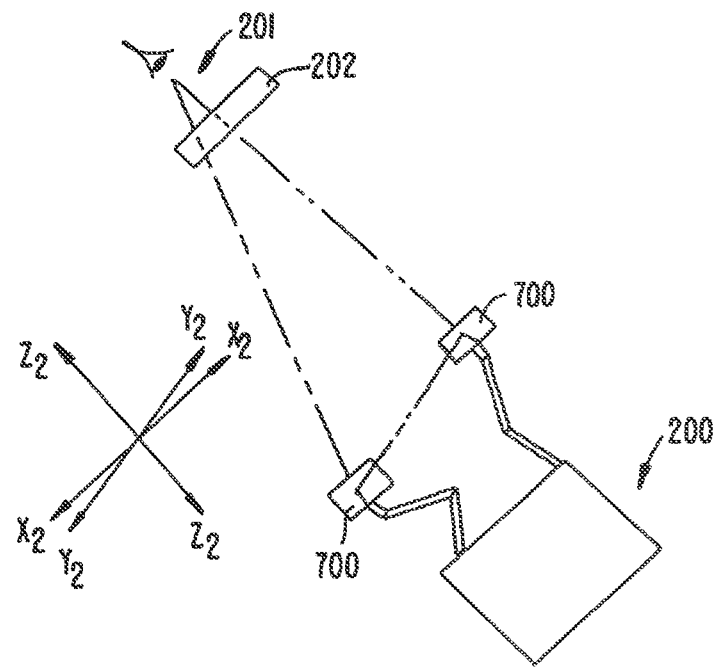
FIG. 2 illustrates a schematic three-dimensional drawing indicating the positions of the end effectors relative to a viewing end of an endoscope and the corresponding positions of master control devices relative to the eyes of an operator.
Figure 2:
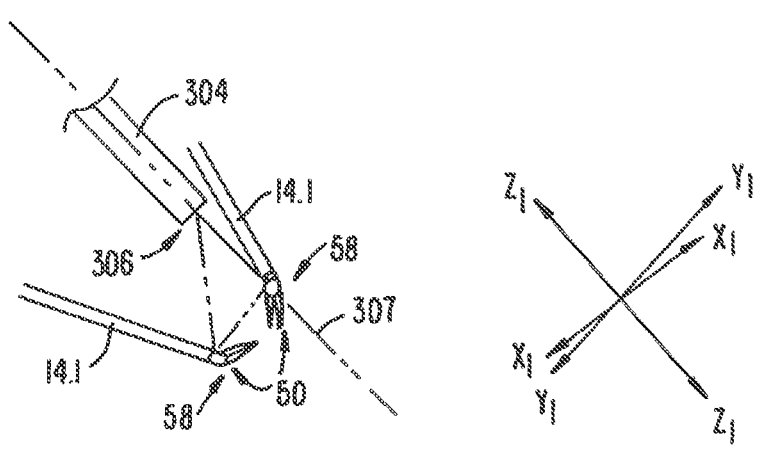

In use, and as schematically indicated in FIG. 2 of the drawings, the surgeon views the surgical site through the display 202. The end effector 58 carried on each tool 14 is caused to perform positional and orientational movements in response to movement and action inputs on its associated master control device. The master control devices are indicated schematically at 700, 700. It will be appreciated that during a surgical procedure images of the end effectors 58 are captured by the endoscope 304 together with the surgical site and are displayed on the display 202 so that the surgeon sees the responsive movements and actions of the end effectors 58 as he or she controls such movements and actions by means of the master control devices 700, 700. The control system (as described in reference to FIG. 10 below) is arranged to cause end effector orientational and positional movement as viewed in the image at the display 202 to be mapped onto orientational and positional movement of a pincher formation of the master control device as will be described in greater detail below.

The operation of the control system of the minimally invasive robotic surgical system will now be described in greater detail. In the description which follows, the control system will be described with reference to a single master control device 700 and its associated robotic arm and surgical instrument 14. The master control device 700 will be referred to simply as "master" and its associated robotic arm and surgical instrument 14 will be referred to simply as "slave."

Figure 3:
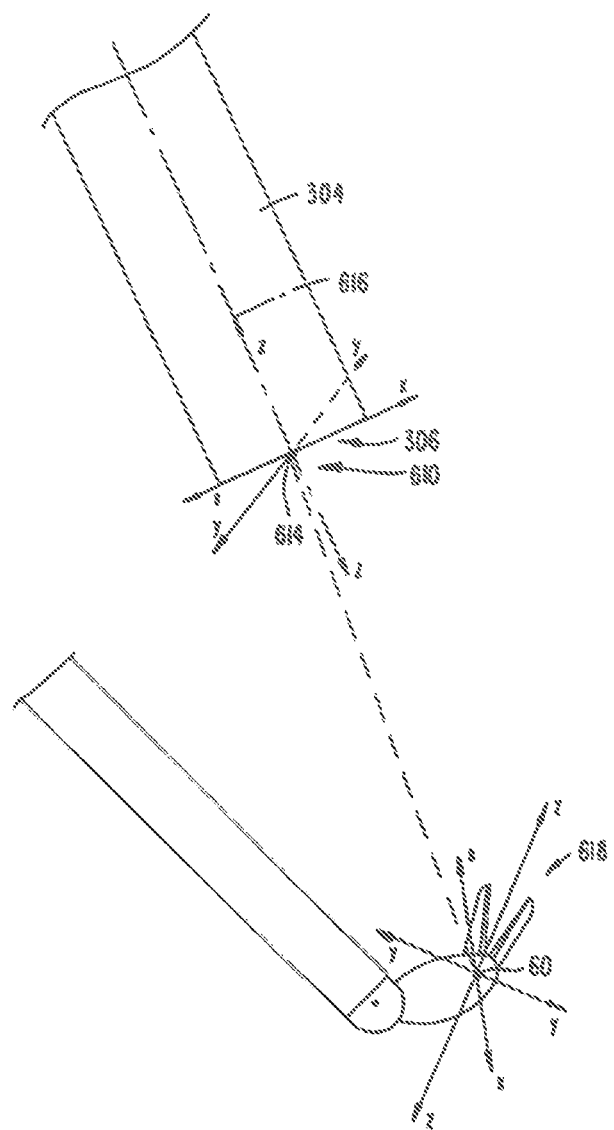
FIG. 3 illustrates a schematic three-dimensional drawing indicating the position and orientation of an end effector relative to an image frame of an image capturing system.

The method whereby control between master movement and corresponding slave movement is achieved by the control system of the minimally invasive surgical system 100 will now be described with reference to FIGS. 2-4 of the drawings in overview fashion. The method will then be described in greater detail with reference to FIGS. 5-15 of the drawings.

Control between master and slave movement is achieved by comparing master position and orientation in an eye Cartesian coordinate reference system (also referred to herein as the "eye frame") with slave position and orientation in a camera Cartesian coordinate reference system (also referred to herein as the "camera frame" or more generally, "image frame"). For ease of understanding and economy of words, the term "Cartesian coordinate reference system" will simply be referred to as "frame" in the rest of this specification including the attached claims. Accordingly, when the master is stationary, the slave position and orientation within the camera frame is compared with the master position and orientation in the eye frame, and if the position and/or orientation of the slave in the camera frame does not correspond with the position and/or orientation of the master in the eye frame, the slave is caused to move to a position and/or orientation in the camera frame at which its position and/or orientation in the camera frame does correspond with the position and/or orientation of the master in the eye frame. In FIG. 3, the camera frame is generally indicated by reference numeral 610 and the eye frame is generally indicated by reference numeral 612 in FIG. 4. Similarly, in a master alignment mode, the slave is stationary and the master is caused to move to a position and/or orientation in the eye frame that corresponds to the slave position and orientation in the camera frame.

When the master is moved into a new position and/or orientation in the eye frame 612, the new master position and/or orientation does not correspond with the previously corresponding slave position and/or orientation in the camera frame 610. The control system then causes the slave to move into a new position and/or orientation in the camera frame 610 at which new position and/or orientation, its position and orientation in the camera frame 610 does correspond with the new position and/or orientation of the master in the eye frame 612.

It will be appreciated that the control system includes at least one, and typically a plurality, of processors which compute new corresponding positions and orientations of the slave in response to master movement input commands on a continual basis determined by the processing cycle rate of the control system. A typical processing cycle rate of the control system under discussion is about 1300 Hz. Thus, when the master is moved from one position to a next position, the corresponding movement desired by the slave to respond is computed at about 1300 Hz. Naturally, the control system can have any appropriate processing cycle rate depending on the processor or processors used in the control system. In one implementation, all real-time servocycle processing is conducted on a DSP (Digital Signal Processor) chip. DSPs are used in this case because of their constant calculation predictability and reproducibility. A DSP from Analog Devices, Inc. of Massachusetts is an acceptable example of such a processor for performing the functions described herein.

The camera frame 610 is positioned such that its origin 614 is positioned at the viewing end 306 of the endoscope 304. Conveniently, the z axis of the camera frame 610 extends axially along a viewing axis 616 of the endoscope 304. Although in FIG. 3, the viewing axis 616 is shown in coaxial alignment with a shaft axis of the endoscope 304, it is to be appreciated that the viewing axis 616 can be angled relative thereto. Thus, the endoscope can be in the form of an angled scope. Naturally, the x and y axes are positioned in a plane perpendicular to the z axis. The endoscope is typically angularly displaceable about its shaft axis. The x, y and z axes are fixed relative to the viewing axis of the endoscope 304 so as to displace angularly about the shaft axis in sympathy with angular displacement of the endoscope 304 about its shaft axis.

To enable the control system to determine slave position and orientation, a frame is defined on or attached to the end effector 58. This frame is referred to as an end effector frame or slave tip frame or simply tool frame, in the rest of this specification, and is generally indicated by reference numeral 618. The end effector frame 618 has its origin at the pivotal connection 60. Conveniently, one of the axes e.g. the z axis, of the frame 618 is defined to extend along an axis of symmetry, or the like, of the end effector 58. Naturally, the x and y axes then extend perpendicularly to the z axis. It will be appreciated that the orientation of the slave is then defined by the orientation of the frame 618 having its origin at the pivotal connection 60, relative to the camera frame 610. Similarly, the position of the slave is then defined by the position of the origin of the frame at 60 relative to the camera frame 610.

Figure 4:
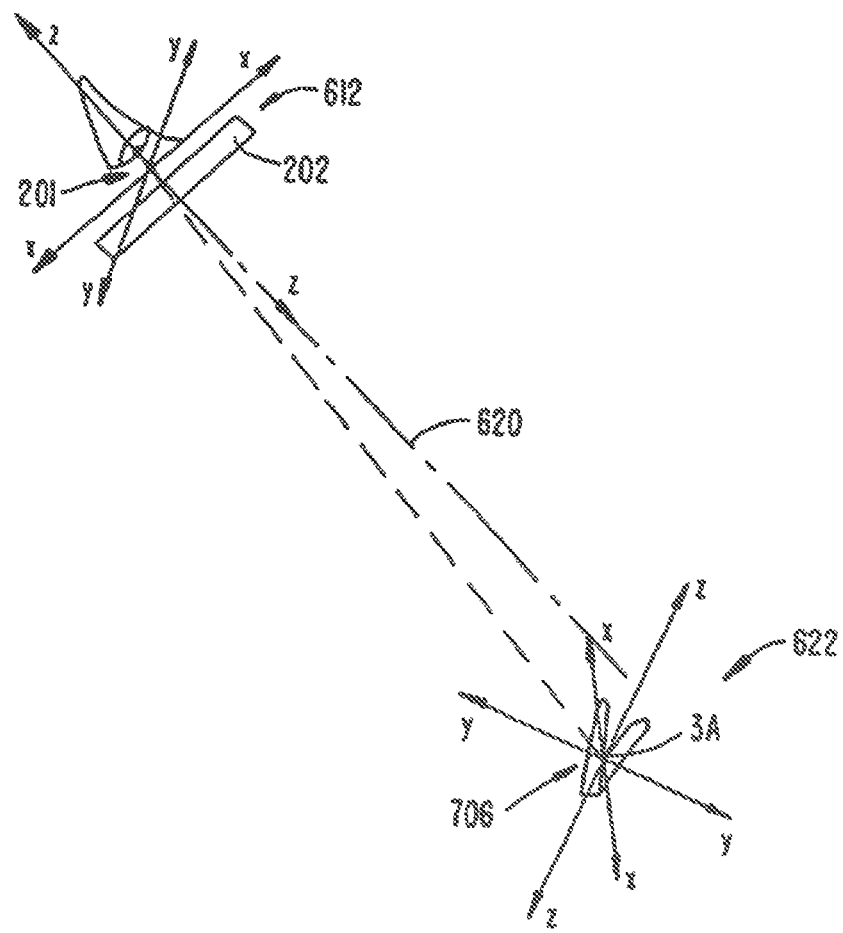
FIG. 4 illustrates a schematic three-dimensional drawing indicating the position and orientation of a pincher formation of a master control device relative to an eye reference system associated with the eyes of an operator of the medical robotic system.

Referring now to FIG. 4 of the drawings, the eye frame 612 is chosen such that its origin corresponds with a position 201 where the surgeon's eyes are normally located when he or she is viewing the surgical site at the display 202. The z axis extends along a line of sight of the surgeon, indicated by axis 620, when viewing the surgical site through the display 202. Naturally, the x and y axes extend perpendicularly from the z axis at the origin 201. Conveniently, the y axis is chosen to extend generally vertically relative to the display 202 and the x axis is chosen to extend generally horizontally relative to the display 202.

To enable the control system to determine master position and orientation within the display frame 612, a point on the master is chosen which defines an origin of a master or master tip frame, indicated by reference numeral 622. This point is chosen at a point of intersection indicated by reference numeral 3A where the axes of rotation of the master intersect. Conveniently, the z axis of the master frame 622 on the master extends along an axis of symmetry of the pincher formation 706 which extends coaxially along the rotational axis 1. The x and y axes then extend perpendicularly from the axis of symmetry 1 at the origin 3A. Accordingly, orientation of the master within the eye frame 612 is defined by the orientation of the master frame 622 relative to the eye frame 612. The position of the master in the eye frame 612 is defined by the position of the origin 3A relative to the eye frame 612.

Figure 5:
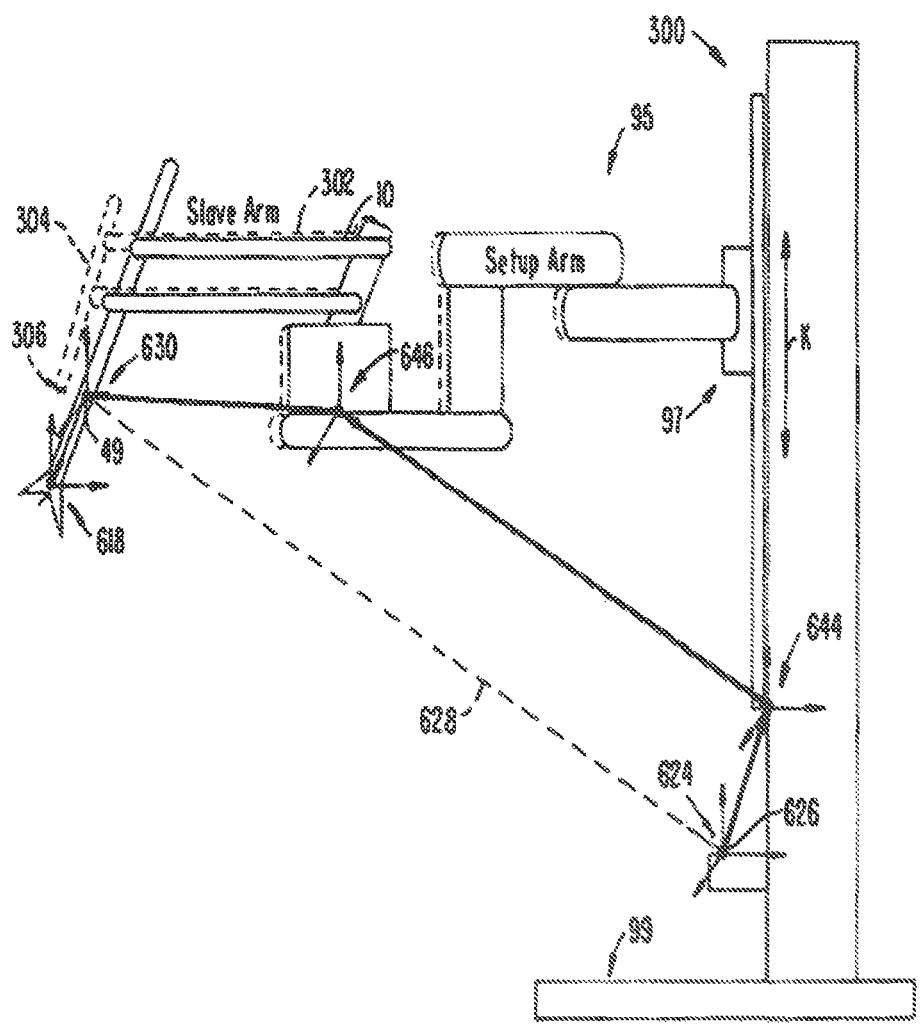
FIG. 5 illustrates a schematic side view of part of a surgical station indicating locations of frames used by a control system to determine the position and orientation of an end effector of a tool relative to an image frame associated with an image capturing system.

How the position and orientation of the slave within the camera frame 610 is determined by the control system will now be described with reference to FIG. 5 of the drawings. FIG. 5 shows a schematic diagram of one of the robotic arm and surgical instrument 14 assemblies mounted on the patient-side cart 300. However, before commencing with a description of FIG. 5, it is appropriate to describe certain previously mentioned aspects of the patient-side cart 300 which impact on the determination of the orientation and position of the slave relative to the camera frame 610.

In use, when it is desired to perform a surgical procedure by means of the minimally invasive surgical system, the patient-side cart 300 is moved into close proximity to a patient requiring the surgical procedure. The patient is normally supported on a surface such as an operating table, or the like. To make allowance for support surfaces of varying height, and to make allowance for different positions of the patient-side cart 300 relative to the surgical site at which the surgical procedure is to be performed, the patient-side cart 300 is provided with the ability to have varying initial setup configurations. Accordingly, the tool slave arms 10, 12, and the endoscope slave arm 302 are mounted on the carriage 97 which is heightwise adjustable, as indicated by arrows K, relative to the base 99 of the cart 300. Furthermore, the tool slave arms 10, 12 and the endoscope slave arm 302 are mounted on the carriage 97 by means of their respective setup arms 95. Thus, the lateral position and orientation of the slave arms 10, 12, 302 can be selected by moving the setup arms 95. Thus, at the commencement of the surgical procedure, the cart 300 is moved into the position in close proximity to the patient, an appropriate height of the carriage 97 is selected by moving it to an appropriate height relative to the base 99 and the surgical instruments 14 are moved relative to the carriage 97 so as to introduce the shafts of the instruments 14 and the endoscope 304 through the ports of entry and into positions in which the end effectors 58 and the viewing end 306 of the endoscope 304 are appropriately positioned at the surgical site and the fulcrums (i.e., pivot points) are coincident with the ports of entry. Once the height and positions are selected, the carriage 97 is locked at its appropriate height and the setup arms 95 are locked in their positions and orientations. Normally, throughout the surgical procedure, the carriage 97 is maintained at the selected height and similarly the setup arms 95 are maintained in their selected positions. However, if desired, either the endoscope or one or both of the instruments can be introduced through other ports of entry during the surgical procedure.

The determination by the control system of the position and orientation of the slave within the camera frame 610 will now be described. It will be appreciated that this is achieved by means of one or more processors having a specific processing cycle rate. Thus, where appropriate, whenever position and orientation are referred to in this specification, it should be borne in mind that a corresponding velocity is also readily determined. The control system determines the position and orientation of the slave within the camera frame 610 by determining the position and orientation of the slave relative to a cart frame 624 and by determining the orientation and position of the endoscope 304 with reference to the same cart frame 624. The cart frame 624 has an origin indicated by reference numeral 626 in FIG. 5.

To determine the position and orientation of the slave relative to the cart frame 624, the position of a fulcrum frame 630 having its origin at the fulcrum 49 is determined within the cart frame 624 as indicated by the arrow 628 in dashed lines. It will be appreciated that the position of the fulcrum 49 normally remains at the same location, coincident with a port of entry into the surgical site, throughout the surgical procedure. The position of the end effector frame 618 on the slave, having its origin at the pivotal connection 60 (as shown in FIG. 3), is then determined relative to the fulcrum frame 630 and the orientation of the end effector frame 618 on the slave is also determined relative to the fulcrum frame 630. The position and orientation of the end effector frame 618 relative to the cart frame 624 is then determined by means of routine calculation using trigonometric relationships.

It will be appreciated that the slave arm 302 of the endoscope 304 is constrained to move in similar fashion to the tool slave arm 10. Thus, the endoscope 304 when positioned with its viewing end 306 directed at the surgical site, also defines a fulcrum coincident with its associated port of entry into the surgical site. The endoscope slave arm 302 can be driven to cause the endoscope 304 to move into a different position during a surgical procedure, to enable the surgeon to view the surgical site from a different position in the course of performing the surgical procedure. It will be appreciated that movement of the viewing end 306 of the endoscope 304 is performed by varying the orientation of the endoscope 304 relative to its pivot center or fulcrum. Operator control of such movement may be performed by switching associations of one or both master control devices 700, 700 from the tools 14, 14 to the endoscope 304. Once the endoscope 304 is moved to the desired position and orientation, the slave arm 304 may be locked in place and associations of the master control devices 700, 700 may be switched back to their respective tools. Alternatively, the foot pedal 105 or other conventional means may be used to position the endoscope 304. The position and orientation of the camera frame 610 within the cart frame 624 is determined in similar fashion to the position and orientation of the slave within the cart frame 624. When the position and orientation of the camera frame 610 relative to the cart frame 624, and the position and orientation of the slave relative to the cart frame 624 have been determined in this manner, the position and the orientation of the slave relative to the camera frame 610 is readily determinable through routine calculation using trigonometric relationships.

Figure 6:
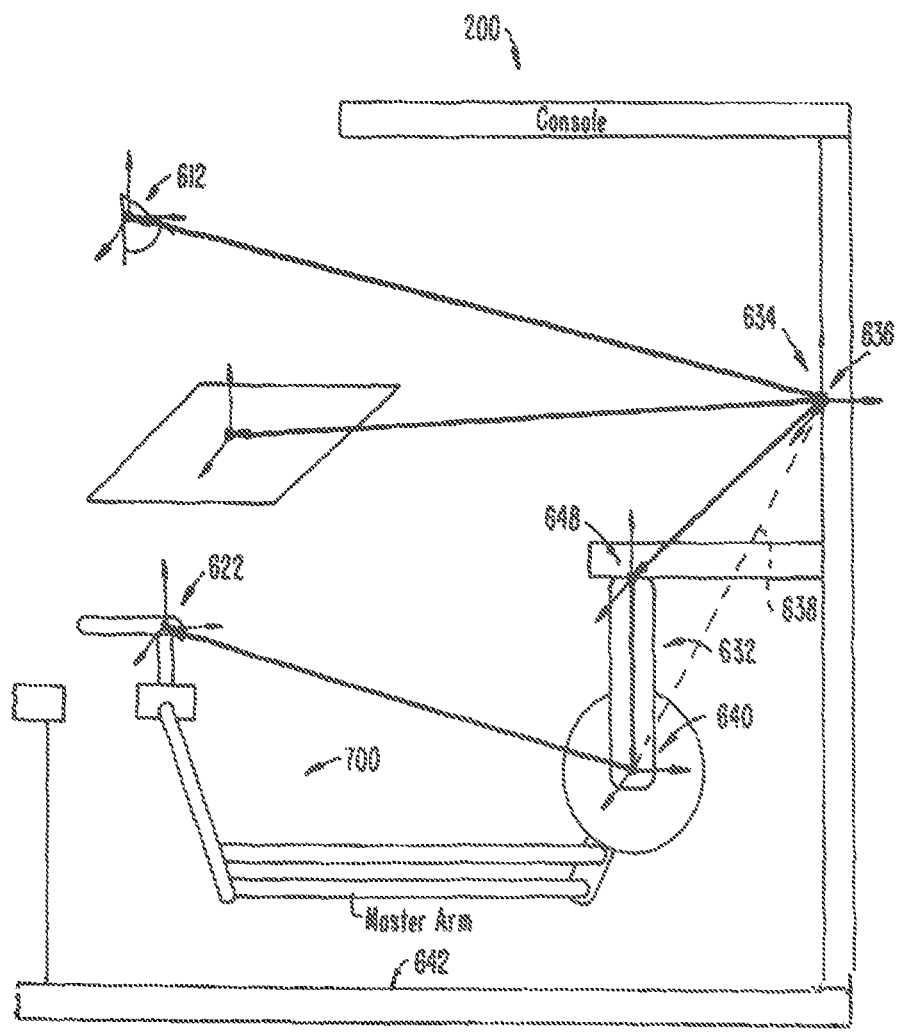
FIG. 6 illustrates a schematic side view of part of a surgeon's workstation 200 indicating locations of frames used by a control system to determine the position and orientation of a pincher formation of a master control device relative to an eye frame associated with the eyes of the surgeon.

How the position and orientation of the master within the display frame 612 is determined by the control system will now be described with reference to FIG. 6 of the drawings. FIG. 6 shows a schematic diagram of one of the master control devices 700 at the operator workstation 200.

The workstation 200 optionally also includes setup arms, as indicated at 632, to enable the general location of the masters 700, 700 to be varied to suit the surgeon. Thus, the general position of the masters 700, 700 can be selectively varied to bring the masters 700, 700 into a general position at which they are comfortably positioned for the surgeon. When the masters 700, 700 are thus comfortably positioned, the setup arms 632 are locked in position and are normally maintained in that position throughout the surgical procedure.

To determine the position and orientation of the master 700, as indicated in FIG. 6, within the eye frame 612, the position and orientation of the eye frame 612 relative to a surgeon's station frame 634, and the position and orientation of the master 700 relative to the surgeon's frame 634 is determined. The surgeon's station frame 634 has its origin at a location which is normally stationary during the surgical procedure, and is indicated at 636.

To determine the position and orientation of the master 700 relative to the station frame 634, a position of a master setup frame 640 at an end of the setup arms 632 on which the master 700 is mounted, relative to the station frame 636, is determined, as indicated by the arrow 638 in dashed lines. The position and orientation of the master frame 622 on the master 700 having its origin at 3A is then determined relative to the master setup frame 640. In this manner, the position and orientation of the master frame 622 relative to the station frame 634 can be determined by means of routine calculation using trigonometric relationships. The position and orientation of the eye frame 612 relative to the station frame 634 is determined in similar fashion. It will be appreciated that the position of the display 202 relative to the rest of the surgeon's workstation 200 can selectively be varied to suit the surgeon. The position and orientation of the master frame 622 relative to the eye frame 612 can then be determined from the position and orientation of the master frame 622 and the eye frame 612 relative to the surgeon station frame 634 by means of routine calculation using trigonometric relationships.

In the manner described above, the control system of the minimally invasive surgical apparatus determines the position and orientation of the end effector 58 by means of the end effector frame 618 in the camera frame 610, and, likewise, determines the position and orientation of the pinchers of the master by means of the master frame 622 relative to the eye frame 612.

As mentioned, the surgeon grips the master by locating his or her thumb and index finger over the pincher formation 706 (see FIG. 4). When the surgeon's thumb and index finger are located on the pincher formation, the point of intersection 3A is positioned inwardly of the thumb and index finger tips. The master frame having its origin at 3A is effectively mapped onto the end effector frame 618, having its origin at the pivotal connection 60 of the end effector 58 as viewed by the surgeon in the display 202. Thus, when performing the surgical procedure, and the surgeon manipulates the position and orientation of the pincher formation 706 to cause the position and orientation of the end effector 58 to follow, it appears to the surgeon that his or her thumb and index finger are mapped onto the fingers of the end effector 58 and that the pivotal connection 60 of the end effector 58 corresponds with a virtual pivot point of the surgeon's thumb and index finger inwardly from the tips of the thumb and index finger. It will be appreciated that depending upon the actual configuration of the pincher formation, in particular the point of intersection of the rotation axes relative to the position of the pincher formation 706, the frame 622 on the master 700 can be offset from the intersection 3A so as to approach a point relative to the surgeon's hand at which point the pivotal connection 60 approximately corresponds.

Accordingly, as the surgical procedure is being performed the position and orientation of the fingers of the end effector track position and orientation changes of the surgeon's thumb and index finger in a naturally intuitive or superimposed fashion. Furthermore, actuation of the end effector 58, namely causing the end effector fingers selectively to open and close, corresponds intuitively to the opening and closing of the surgeon's thumb and index finger. Thus, actuation of the end effector 58 as viewed in the display 202 is performed by the surgeon in a naturally intuitive manner, since the pivot point 60 of the end effector 58 is appropriately mapped onto a virtual pivot point between the surgeon's thumb and index finger.

Figure 7:
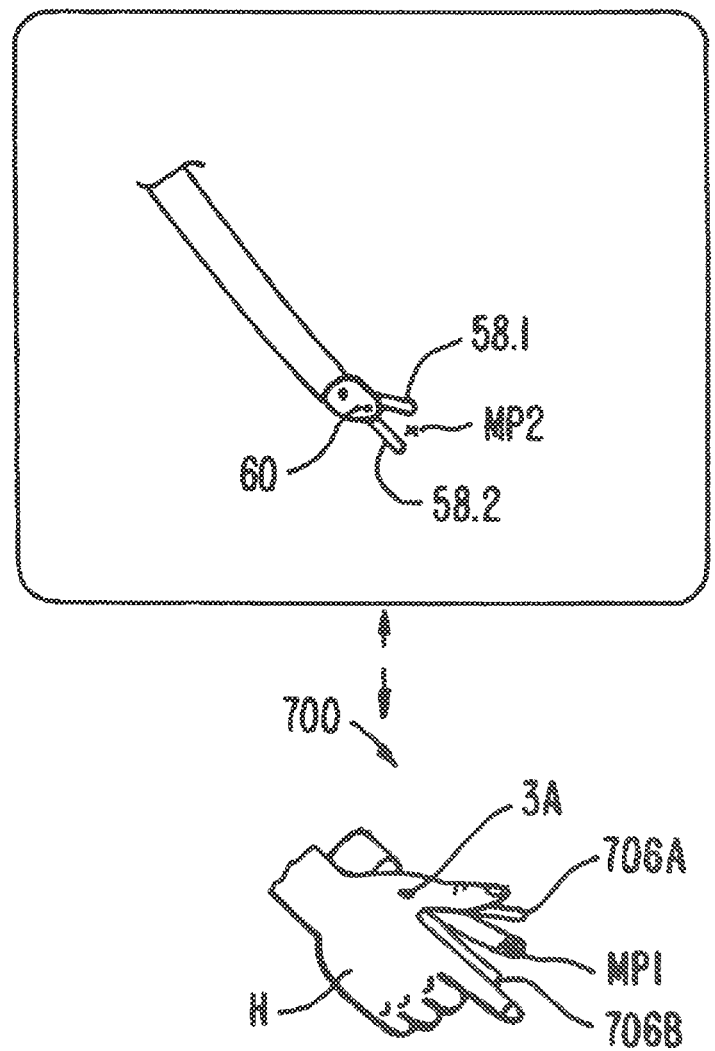
FIGS. 7-9 schematically illustrate corresponding mapping locations on the surgeon's hand, on the master control device, and on the end effector of a tool and methods for their selection.

It will be appreciated that the end effector frame 618 can, where appropriate, be offset relative to the pivotal connection 60. Thus, for example, if the end effector (as shown in the display) has fingers of a relatively long length, the origin of the end effector frame can be offset in a direction toward the end effector finger tips. It will also be appreciated that by using positional and/or orientational offsets between the master frame 622 and the intersection 3A, as well as between the end effector frame 618 and the pivotal connection 60, the mapping of the pincher formation 706 onto the end effector 58 may be shifted, for example to map the tips of the pincher formation onto the tips of the end effector. These alternative mappings are illustrated in FIG. 7.

Generally, a first pincher element 706A will be substantially connected to a first end effector element 58.1, while a second pincher element 706B is substantially connected to a second end effector element 58.2. Optionally, point 3A (which is ideally near the center of rotation of the gimbal structure of master 700, 706A, and 706B), adjacent the pivotal connection between the pincher elements, may be substantially connected with pivotal connection 60 on the slave. This also effectively provides a substantial connection between the pivot point on the surgeon's hand H and pivotal connection 60, as the surgeon will often grip the master with the hand's pivot point (at the base of the surgeon's finger and thumb) disposed along the pivot point of the pincher. Alternatively, midpoint MP1 disposed between the tips of the pincher elements may be substantially connected to midpoint MP2 disposed between the tips of the end effector elements. Each of the higher levels of connection described herein may optionally be provided by this mapping.

Figure 8:
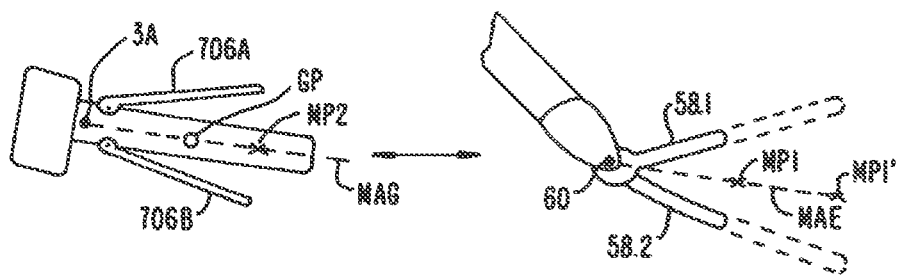
Figure 9:
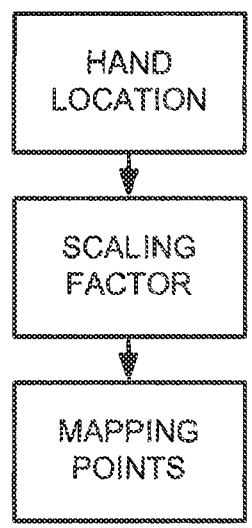

FIGS. 8 and 9 more clearly illustrate corresponding mapping points between the handle of the master controller and end effector of the slave, while FIG. 9 schematically illustrates method steps for selecting these corresponding mapping points. In general, interchangeable end effectors having different end effector element lengths may be accommodated by varying the mapping point of the handle or the end effector. Such variation in mapping points may also be used when the magnification of the image shown at the display changes significantly. For example, substantial connection of pivotal connection 60 of the end effector and intersection 3A of the handle may be appropriate when the end effector is shown at a first magnification, but may be inappropriate when magnification of the end effector is increased significantly, or when an alternative end effector having longer end effector elements is attached to the slave. In either circumstance, it may be appropriate to alter the master/slave interaction to substantially connect midpoint MP2 of the master to midpoint MP1' of the end effector, as illustrated in FIG. 8.

As a preliminary matter, it is beneficial in robotic surgery systems to provide a master controller having a gimbal point GP adjacent the handle to be gripped by the surgeon. This avoids large master inertia when the surgeon rapidly rotates the handle, as often occurs during surgical procedures. By having a master which has multiple degrees of freedom intersecting at the gimbal point GP (ideally having three orientational degrees of freedom intersecting at the gimbal point), and by having the gimbal point coincident with the handle, inertia of rapid rotational movements at the master can be quite low.

As described above, it is often beneficial to coordinate movements of the slave so that an image of pivotal connection 60 of the slave appears substantially connected to pincher formation pivot point 3A between the pincher or grip elements 706A, 706B. However, when end effector elements 58.1, 58.2 extend a considerable distance beyond pivotal connection 60 (as shown in the display adjacent the master controller), the surgeon may feel that manipulation of these long end effector elements from the distant pivotal connection becomes awkward. Similarly, when manipulating a single end effector element such as a scalpel which is much longer (as displayed at the master control station) than the master handle, the surgeon may be given the impression of cutting with a long-handled sword, rather than an easily controlled scalpel. As described above, one alternative to overcome an awkward disparity in grip/end effector lengths is to map the surgical workspace and master controller workspace together so that the midpoints MP1, MP2 between the end effector jaw ends and the handle grip member ends are substantially connected. By mapping the surgical and master workspace so that these midpoints are substantially connected, the surgeon can coordinate movement using the end effector despite significant differences in length between the end effector elements and the grip elements.

The mapping point need not be limited to any particular point. In the exemplary embodiment, a middle axis of the grip members MAG is generally defined midway between pincher elements 706A, 706B, while a similar middle axis of the end effector MAE is defined midway between the end effector elements 58.1, 58.2. The mapping point (or point of substantial connection) of the master will be disposed along gripping middle axis MAG, ideally in a range from intersection 3A to midpoint MP2. Similarly, the mapping or substantial connection point of the end effector will be disposed along middle axis MAE, ideally in a range from pivotal connection 60 to midpoint MP1.

FIG. 9 schematically illustrates a method for determining the location of the substantially connected mapping points along the handle and end effector. First, the location of the surgeon's hand along the master handle is reviewed to determine the position of the surgeon's fingers relative to the gimbal point GP. In one embodiment, the offset distance between a location of the surgeon's fingertips and the gimbal point GP defines an offset distance. This offset distance is scaled using a scaling factor, typically using a ratio between a length of the grip members and the length of the end effector elements, a magnification of the display, or the like. For example, using numbers typical of the exemplary robotic surgery system, the offset distance is scaled by multiplying it by one-third, as the grip members typically have a length of about three times the end effector element lengths. This scaling factor may change with tool changes (when end effectors having longer or shorter end effector elements are used), or the like. The location of the mapping points on the slave can then be calculated, for example, at a position offset from midpoint MP1 toward pivotal connection 60 along the end effector middle axis MAE by the scaled offset distance. This mapping point of the end effector may then be substantially connected to gimbal point GP of the master.

It will be appreciated that the cart frame 624 can be chosen at any convenient location in which its origin corresponds with a location on the cart 300 which does not vary relative to its base 99. The surgeon's station frame 634 can likewise be chosen at any convenient location such that its origin is located at a position which does not vary relative to a base 642 thereof. Furthermore, to determine the position and orientation of the camera frame 610 relative to the cart frame 624, use can be made of a plurality of different intermediate frame paths. To determine the position and orientation of the end effector frame 618 relative to the cart frame 624 use can also be made of a plurality of different intermediate frame paths.

However, it has been found that if the intermediate frame paths are appropriately selected, the control system is then arranged to be readily adaptable to accommodate modular replacement of modular parts having characteristics different than the characteristics of the modular parts being replaced. It will be appreciated that selecting intermediate frames also eases the computational process involved in determining master and slave position and orientation.

Referring again to FIG. 5, the cart frame is chosen at 624, as already mentioned. It will be appreciated that determining the position of the fulcrum frame 630 relative to the cart frame 624 is achieved through appropriately positioned sensors, such as potentiometers, encoders, or the like. Conveniently, the fulcrum frame position 630 relative to the cart frame 624 is determined through two intermediate frames. One of the frames is a carriage guide frame 644 which has its origin at a convenient location on a guide along which the carriage 97 is guided. The other frame, an arm platform frame indicated at 646 is positioned at an end of the setup joint arm 95 on which the slave arm 10 is mounted. Thus, when slave position and orientation is determined relative to the cart frame 624, the carriage guide frame 644 position relative to the cart frame 624 is determined, then the platform frame 646 position relative to the carriage guide frame 644 is determined, then the fulcrum frame 630 relative to the platform frame 646 is determined, and then the slave orientation and position relative to the fulcrum frame 630 is determined, thereby determining the slave position and orientation relative to the cart frame 624. It will be appreciated that the slave position and orientation relative to the cart frame 624 is determined in this manner for each arm 10 and in similar fashion for the camera frame 610, through its arm 302, relative to the cart frame 624.

Referring to FIG. 6, the position and orientation of the master control is determined by determining the position of a base frame 648 relative to the surgeon's station frame 634, then determining the position of the platform frame 640 relative to the base frame 648, and then determining master position and orientation relative to the platform frame 640. The position and orientation of the master frame 622 relative to the surgeon's station frame 634 is then readily determined through routine calculation using trigonometric relationships. It will be appreciated that the position and orientation of the other master frame relative to the surgeon workstation 200 frame 634 is determined in a similar fashion.

Referring to FIG. 5, by choosing the frames as described, the setup joint 95 can be replaced with another setup joint while the same robotic arm is used. The control system can then be programmed with information, e.g., arm lengths and/or the like, relating to the new setup joint only. Similarly, the slave arm 10 can be replaced with another arm, the control system then requiring programming with information, e.g., fulcrum position and/or the like, relating to the new slave arm only. It will be appreciated that in this way the endoscope slave arm 302 and its associated setup joint can also be independently replaced, the control system then requiring programming of information relating only to the part being replaced. Furthermore, referring to FIG. 6, the setup joint and master control can also independently be replaced, the control system requiring programming of information relating to the characteristics of the new part only.

Figure 10:
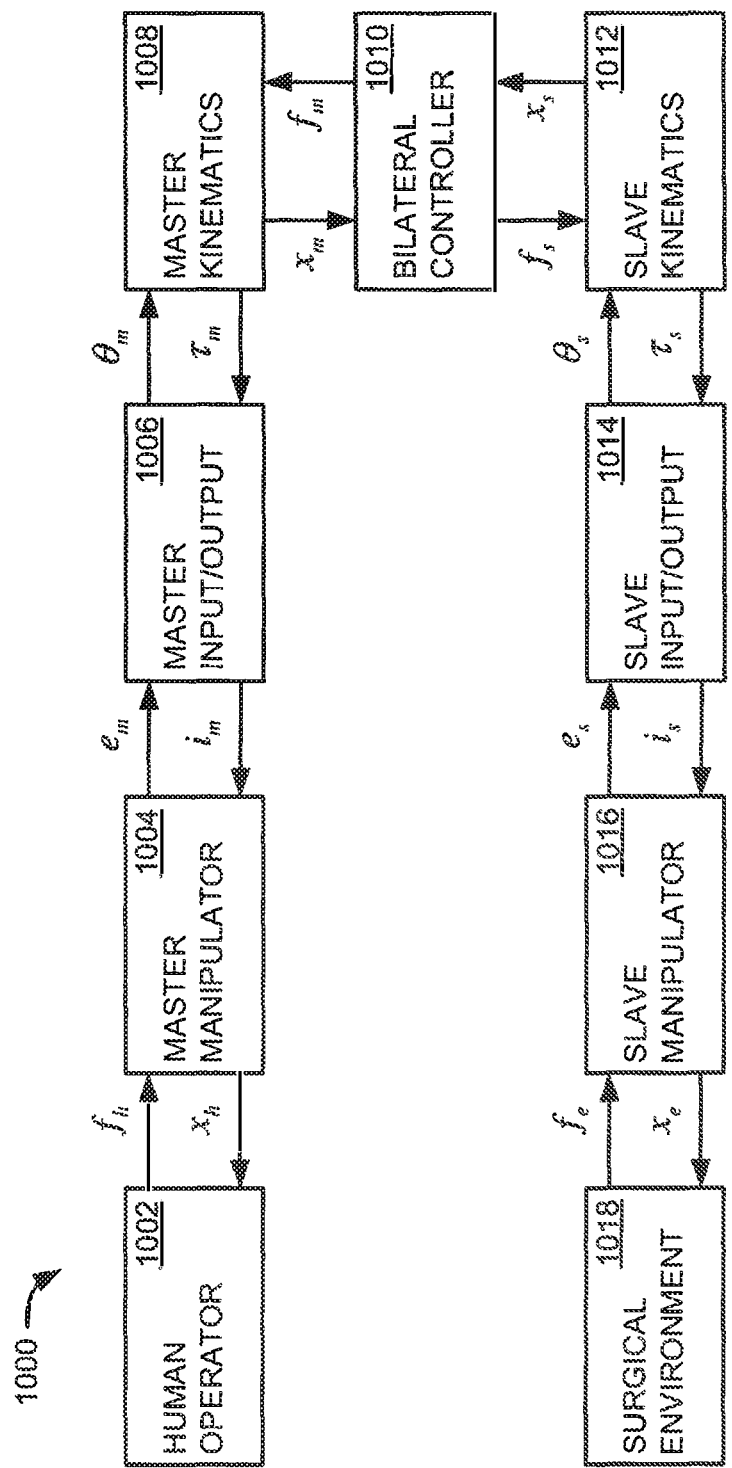
FIG. 10 illustrates a block diagram of a high level control architecture model of a master/slave robotic system.

FIG. 10 schematically illustrates a high level control architecture for a master/slave robotic system 1000. Beginning at the operator input, a surgeon 1002 moves an input device of a master manipulator 1004 by applying manual or human forces fh against the input device. Encoders of master manipulator 1004 generate master encoder signals em which are interpreted by a master input/output processor 1006 to determine the master joint positions θm. The master joint positions are used to generate Cartesian positions of the input device of the master xm relative to the eye frame using a master kinematics model 1008.

Starting now with the input from the surgical environment 1018, the tissue structures in the surgical workspace will impose forces fe against a surgical end effector (and possibly against other elements of the tool and/or manipulator). Environmental forces fe from the surgical environment 1018 alter position of the slave manipulator 1016, thereby altering slave encoder values θs transmitted to the slave input/output processor 1014. Slave input/output processor 1014 interprets the slave encoder values to determine joint positions θs, which are then used to generate Cartesian slave position signals xs relative to the camera frame according to the slave kinematics processing block 1012.

The master and slave Cartesian positions xm, xs are input into bilateral controller 1010, which uses these inputs to generate the desired Cartesian forces to be applied by the slave fs so that the surgeon can manipulate the slave as desired to perform a surgical procedure. Additionally, bilateral controller 1010 uses the Cartesian master and slave positions xm, xs to generate the desired Cartesian forces to be applied by the master fm so as to provide force feedback to the surgeon.

In general, bilateral controller 1010 will generate the slave and master forces fs, fm by mapping the Cartesian position of the master in the master controller workspace with the Cartesian position of the end effector in the surgical workspace according to a master-tool transform which takes into account a desired scale factor and offsets. The scale factor specifies a desired scale change between master control input movement and responsive slave output movement. The offsets are taken into account so that the position and orientation of the end effector frame 618 relative to the camera frame 610 are aligned with the position and orientation of the master frame 622 relative to the eye frame 612.

The control system 1000 will derive the master-tool transform in response to state variable signals provided from the imaging system so that an image of the end effector in a display appears substantially connected to the input device. These state variables will generally indicate the Cartesian position of the field of view from the image capture device, as supplied by the slave manipulators supporting the image capture device. Hence, coupling of the image capture manipulator and slave end effector manipulator is beneficial for deriving this transform. Clearly, bilateral controller 1010 may be used to control more than one slave arm, and/or may be provided with additional inputs.

Based generally on the difference in position between the master and the slave in the mapped workspace, bilateral controller 1010 generates Cartesian slave force fs to urge the slave to follow the position of the master. The slave kinematics 1012 are used to interpret the Cartesian slave forces fs to generate joint torques of the slave τs which will result in the desired forces at the end effector. Slave input/output processor 1014 uses these joint torques to calculate slave motor currents is, which reposition the slave xe within the surgical worksite.

The desired feedback forces from bilateral controller are similarly interpreted from Cartesian force on the master fm based on the master kinematics 1008 to generate master joint torques TS. The master joint torques are interpreted by the master input/output controller 1006 to provide master motor current im to the master manipulator 1004, which changes the position of the hand held input device xh in the surgeon's hand.

It will be recognized that the control system 1000 illustrated in FIG. 10 is a simplification. For example, the surgeon does not only apply forces against the master control device, but also moves the handle within the master workspace. Similarly, the motor current supplied to the motors of the master manipulator may not result in movement if the surgeon maintains the position of the master controller. Nonetheless, the motor currents do result in tactile force feedback to the surgeon based on the forces applied to the slave by the surgical environment. Additionally, while Cartesian coordinate mapping is used, the use of spherical, cylindrical, or other frames may provide at least some of the advantages of the invention.

In the foregoing, it is assumed that all relevant dimensions and angles in the system are known for determining the master-tool transform so that it may be used in controlling movement of the end effector 58 of the tool 14 in response to movement of its associated master control device 700. However, in some circumstances one or more static lengths or angles of the kinematics structure may not be known or readily determinable.

Figure 11:
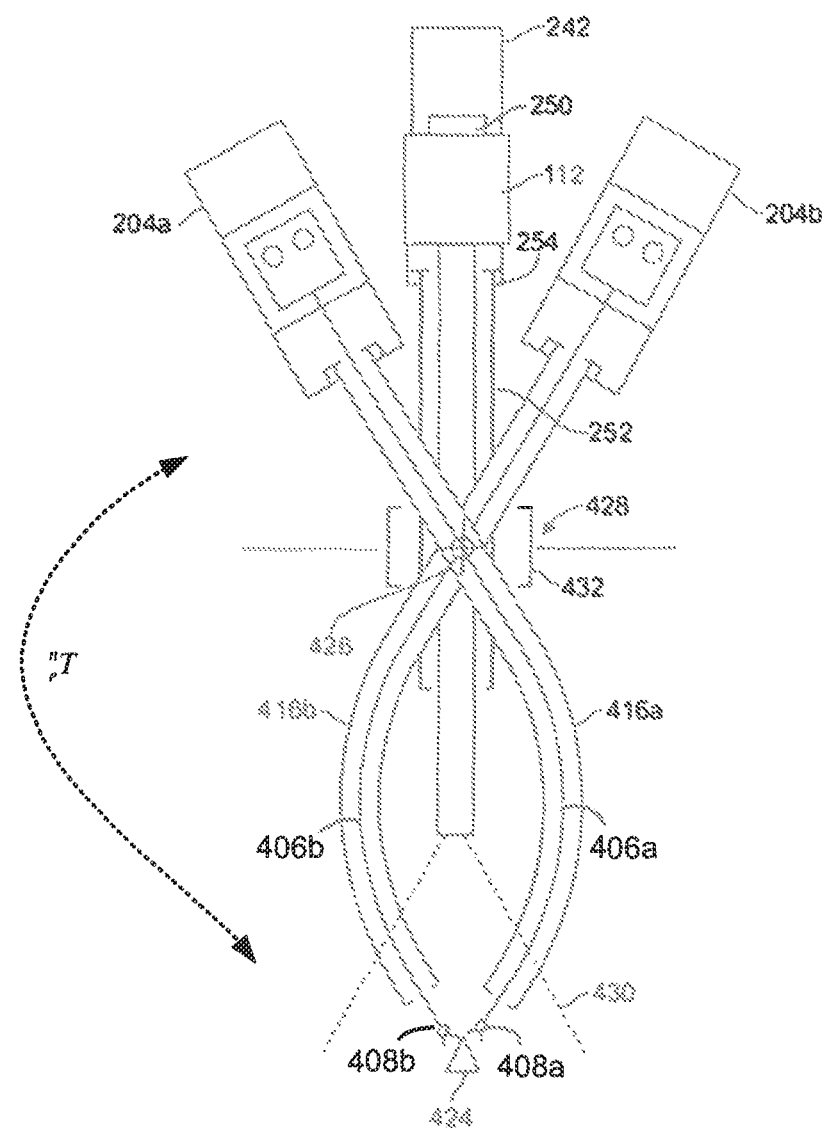
FIG. 11 illustrates a schematic side view of left and right tools inserted along with an endoscope through curved cannulas so that the tools and endoscope pivot about a common pivot point located at a common entry port.

As one example where one or more such lengths and/or angles are not known, FIG. 11 illustrates a schematic side view of tools 406a, 406b inserted along with an endoscope 112 through a common entry port 428 into a patient. The tools 406a, 406b are inserted through and extend out of opposingly curved cannulas (or more generally, tool guides) 416a, 416b so that their end effectors 408a, 408b are positioned to perform a procedure at a work site 424 as shown. The endoscope 112, on the other hand, is inserted through and extends out of a straight cannula 252 so that the end effectors 408a, 408b and work site 424 are in its field of view 430. Each of the cannulas 416a, 416b, 252 is inserted into and supported by a port feature 432 at the entry port 428.

The tools 406a, 406b and endoscope 112 are coupled to their respective manipulators 204a, 204b and 242 (only partially shown) that actuate their movements relative to their respective fulcrums (also referred to in this case as remote centers of motion) 426, each of which is positioned to be approximately at the entry port 428 as shown. Each of the tools 406a, 406b has a flexible shaft so that it may bend to accommodate its rigid single piece curved cannula. To perform different procedures and/or to accommodate different tools, different cannulas having different curvatures and lengths may be used. Additional details of such curved cannulas and systems that use them may be found, for example, in U.S. application Ser. No. 12/618,583 (filed Nov. 13, 2009; entitled "Curved Cannula Surgical System"), which is incorporated herein by this reference. It is to be appreciated, however, that cannulas having difference curvatures and lengths result in different positions and orientations of the tool's end effector frame as the end effector extends out of the distal end of such curved cannula.

Although an operator may manually provide to the system an identification of the curved cannula being used at the time so that the system may use known dimensional information for the cannula to determine the position and orientation of the tool's end effector frame, sometimes the operator may not be aware of which cannula is being used. Thus, in such a case, the unknown position and orientation of the end effector frame must be determined by the system in some manner in order to properly control movement of the tool in response to movement of its associated master control device.

Figure 12:
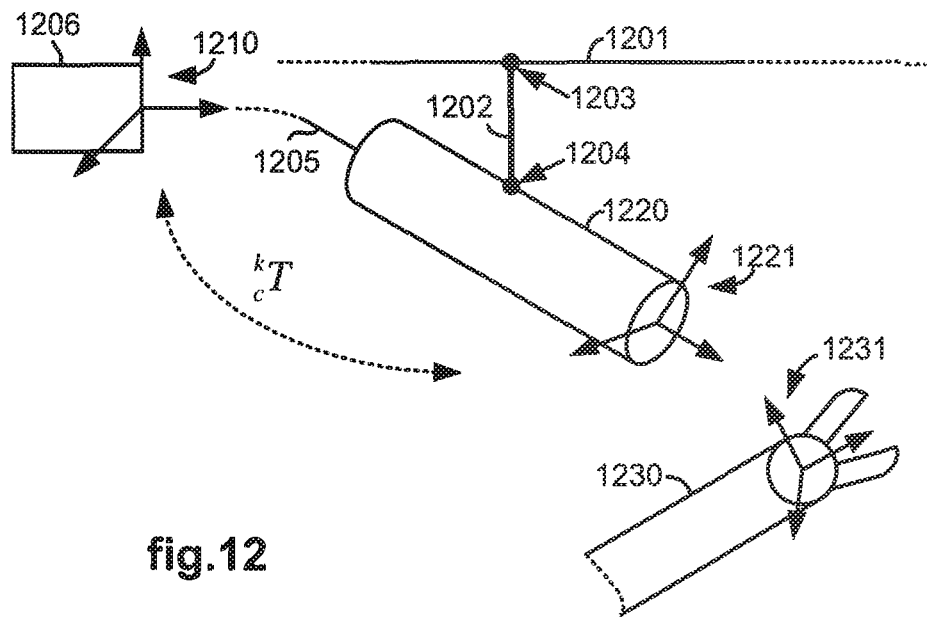
FIG. 12 illustrates a schematic side view of an endoscope tethered at a work site to view a tool.

As another example where one or more such lengths and/or angles are not known, FIG. 12 illustrates a schematic side view of a tethered camera 1220 which captures images of an end effector of a tool 1230 while the end effector is being used to perform a procedure at a work site. A cord 1202 is attached at one end 1204 to the camera 1220 and the other end 1203 to the patient structure 1201 by conventional means. The position and/or orientation of the camera tip may be changed by a mechanical element 1206 pulling on the camera's tether 1205. Movement of the mechanical element 1206 is actuated by a slave manipulator. In this case, although the position and orientation of the frame 1210 of the mechanical element 1206 may be determined by sensors along its kinematic chain, the lengths of the tether 1205 and cord 1202 and the change in position and orientation of the camera 1220 resulting from pulling on the tether 1205 may not be known by the surgeon or system. Thus, in such a case, the unknown position and orientation of the camera frame 1221 must be determined by the system in some manner in order to properly control movement of the tool relative to the camera frame 1221 in response to movement of its associated master control device. Signals from the camera 1220 may be transmitted through fiber optic cables disposed within or alongside the tether 1205 or alternatively, they may be transmitted wirelessly.

Figure 13:
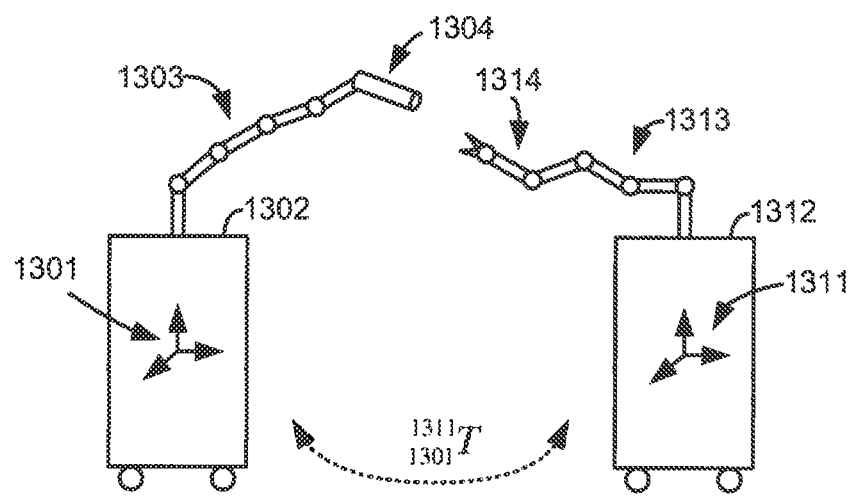
FIG. 13 illustrates a schematic side view of movable structures for respectively positioning a robotically controlled tool and image capturing system at a work site.

As yet another example where one or more such lengths and/or angles are not known, FIG. 13 illustrates a schematic side view of movable structures 1312, 1302 for respectively positioning a robotically controlled tool 1314 and image capturing system 1304 at a work site. In this case, the system is able to determine the position and orientation of the image reference frame of the image capturing system 1304 relative to a frame 1301 associated with the movable structure 1302 by using joint position sensors and known dimensions of the robotic arm 1303. It is also able to determine the position and orientation of the tool frame relative to a frame 1311 associated with the movable structure 1312 by using joint position sensors and known dimensions of the robotic arm 1313. However, the distance and/or relative orientation between the movable structures 1312, 1302 may not be known. Thus, in such a case, the unknown distance and/or relative orientation between the movable structures 1312, 1302 or alternatively between their respective frames 1311, 1301 must be determined by the system in some manner in order to properly control movement of the tool 1314 relative to the camera frame in response to movement of tool 1314's associated master control device.

In the present invention, rather than estimating the unknown lengths and/or angles for determining the master-tool transform, an unknown position and orientation of a frame corresponding to the unknown length and/or angle is estimated instead by estimating a transform to the unknown position and orientation from known positions and orientations of other frames. For examples, in reference to FIG. 11, the unknown position and orientation of the end effector frame is determined by the processor 102 estimating a transform $_e^m T$ which transforms points in an end effector frame to corresponding points in a slave manipulator frame; in reference to FIG. 12, the unknown position and orientation of the camera frame is determined by the processor 102 estimating a transform $_c^k T$ which transforms points in the image frame 1221 to corresponding points in a mechanical element frame 1210; and in reference to FIG. 13, the unknown distance and/or relative orientation between the movable structures 1302, 1312 is determined by the processor 102 estimating a transform $_{1301}^{1311}T$ which transforms points in the movable structure frame 1301 to corresponding points in the movable structure frame 1311 which is assumed in this case to be a fixed frame. For details on the computation, manipulation, and nomenclature of such transforms, see, e.g., John J. Craig, Introduction to Robotics Mechanics and Control, 2nd Edition, Addison-Wesley Publishing Company, Inc., 1989.

Figure 14:
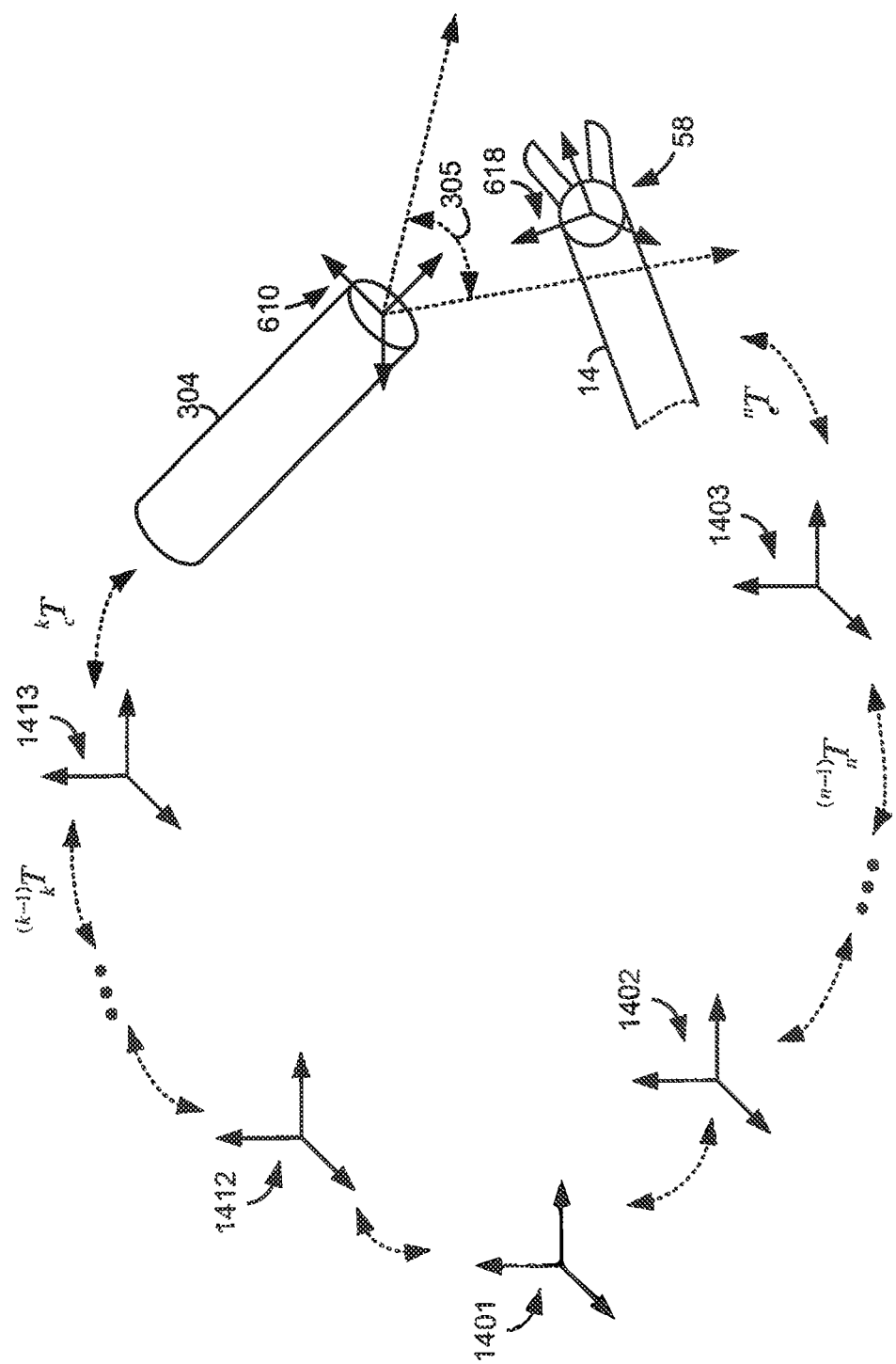
FIG. 14 illustrates a schematic diagram of image frame transforms used for transforming points in an image frame to a fixed frame and tool frame transforms used for transforming points in a tool frame to the fixed frame.

A framework for describing the invention is illustrated in FIG. 14 which shows a generalized schematic diagram of image frame transforms (e.g., $_k^{(k-1)}T$, $_c^kT$) and tool transforms (e.g., $_n^{(n-1)}T$, $_e^nT$). The image frame transforms in this case are used for transforming or mapping points between an image frame 610, intermediate frames (e.g., 1412, 1413), and a fixed frame 1401. Likewise, the tool frame transforms are used for transforming or mapping points between a tool frame 618, intermediate frames (e.g., 1402, 1403), and the fixed frame 1401.

Figure 15:
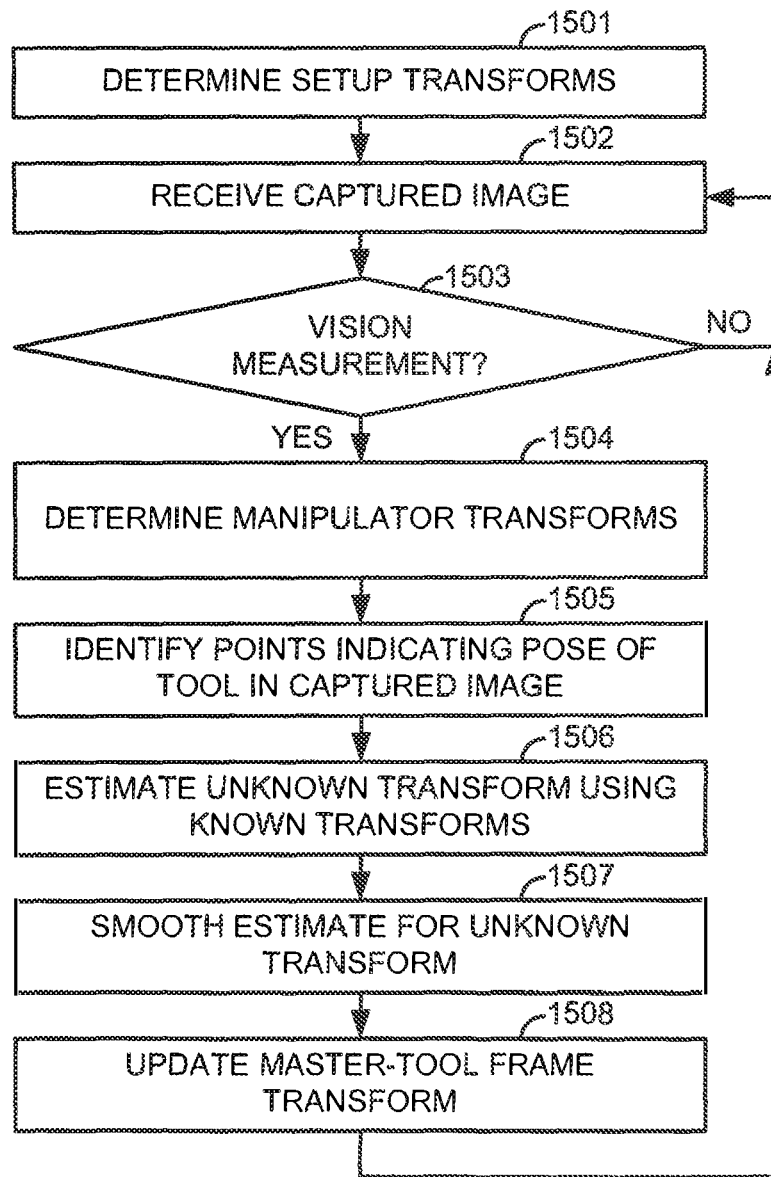
FIG. 15 illustrates a flow diagram of a method for estimating an unknown frame transform for commanding movement of a tool in response to movement of a master control device.

FIG. 15 illustrates, as an example, a flow diagram of a method for estimating and periodically updating a master-tool frame transform for controlling movement of a tool in response to movement of an associated master control device in a robotic system. In 1501, a processor implementing the method determines setup transforms such as those related to the setup arm 95 for the cart 300, as described in reference to FIG. 5, which is locked in place after the tool 14 is properly positioned in the entry port to perform a procedure at a work site. Since these transforms do not change in this example during the procedure being performed by the tool, it is not necessary for them to be continually updated as part of the processing loop.

In 1502, the processor receives access to information of an image that has been captured by an image capturing system such as the endoscope 304. As an example, the image information may be stored in a frame buffer from which it is to be displayed on the display 204. In 1503, a determination is made whether a vision measurement is to be performed. It is to be appreciated that although the frame buffer is updated periodically to refresh images being displayed on the display 204, a vision measurement need not be performed each time the frame buffer is updated. Therefore, a vision measurement might be performed periodically after a number of frame buffer refresh times.

If the determination in 1503 is NO, then the processor loops back to 1502. On the other hand, if the determination is YES, then the processor proceeds to 1504 where the processor determines the slave manipulator transforms such as those related to the slave arm 10 coupled to the cart 300 as described in reference to FIG. 5, by using sensed joint and/or linkage positions and known dimensions of the slave arm 10. Although 1504 is shown as being performed each time a vision measurement is performed, it is to be appreciated that a slave manipulator transform need only be determined if the corresponding slave manipulator has been moved (translationally or orientationally) since the last time its slave manipulator transform has been determined. For example, if the position and orientation of the image capturing device 304 is held fixed while the tool 14 is being used to perform a procedure at a work site, then it is not necessary to determine its slave manipulator transform(s) more than once during the period it is being held in the fixed position and orientation.

In 1505, the processor identifies pose indicating points of the end effector and/or other kinematic structure in the captured image. To do this, measurements of features related to the position and orientation (i.e., pose) of the end effector and/or other kinematic structure are made from the images. The measurements can be in different forms depending on the type of camera being used to capture the image (e.g., monocular or stereo) and the types of image features or fiducial markers being identified in the captured image.

If a stereo camera is being used, the depth of a point can be determined by the process of stereo triangulation, given the intrinsic parameters of the two cameras and their relative pose. Distinctive features are needed to separate themselves from other image features generated by another part of the tool, robot arm, and background. Fiducial markers are used in order to create distinctive features. The fiducial markers can be distinctive in spectral property (e.g., color), in shape, in geometric configuration, or in their combinations. Examples of such markers and their use are described in U.S. Patent Application Pub. No. US 2010/0168562 A1 (filed Apr. 23, 2009; entitled "Fiducial Marker Design and Detection for Locating Surgical Instrument in Images") and U.S. Patent Application Pub. No. US 2010/0168763 A1 (filed Apr. 23, 2009; entitled "Configuration Marker Design and Detection for Instrument Tracking"), both of which are incorporated herein by reference.

If a monocular camera is used, the measurements are inherently in the two-dimensional (2D) image domain. However, having certain knowledge of the tool and/or fiducial marker(s) on the tool can still make three-dimensional (3D) measurements possible. Given the intrinsic parameters of the camera, the 3D pose of an object of known geometry can be recovered with 2D-to-3D point correspondences by a process called pose estimation, see, e.g., David A. Forsyth and Jean Ponce, Computer Vision: A Modern Approach, Prentice Hall, 2003. Pose or partial pose of special geometric shapes (e.g., circles, spheres, cylinders, and cones) can be computed from their outlines, see, e.g., Yiu C. Shiu and Hanqi Zhuang, "Pose Determination of Cylinders, Cones, and Spheres from Perspective Projections," Applications of Artificial intelligence X: Machine Vision and Robotics, Proceedings SPIE, Vol. 1708, pp. 771-782, March 1992. Such geometric shapes are common in surgical instruments or tools.

If the 2D measurements in the image domain cannot be directly converted into 3D using the above techniques, then the 3D pose may be estimated instead. In this case, the image projection $u_i=[u_i, v_i]^t$ of a 3D point $c_{pi}=[c_{xi}, c_{yi}, c_{zi}]^T$ may be computed by:

$$\begin{cases} u_i = f_x \dfrac{cxi}{czi} + u_0 \\ v_i = f_y \dfrac{cyi}{czi} + v_0 \end{cases} \quad (1)$$

wherein $f_x$ and $f_y$ are the focal length in horizontal and vertical directions of an imager respectively, and $u_0$ and $v_0$ are the principal point.

In 1506, the processor estimates an unknown transform using the transforms and other information determined in 1504 and 1505. In doing so, it uses the following transform equation:

$$_c^eT = {_w^eT} \, _c^wT \quad (2)$$

where $_c^eT$ is the image (or camera "c") frame to tool (or end effector "e") frame transform (which may be determined mathematically after identifying pose indicating points of the end effector in the image frame in 1505), $_c^w T$ is the image frame to fixed (or world "w") frame transform, and $_w^e T$ is the inverse of tool frame to fixed frame transform.

Both transforms $_c^w T$ and $_w^e T$ may involve a chain of transforms. As an example, referring to FIG. 14, if frame 1401 is the fixed frame (i.e., a stationary frame), then the chain of transforms from the tool frame to the fixed frame (referred to herein as the "tool frame transforms") includes the frame 618 to frame 1403 transform at its start and the frame 1402 to frame 1401 transform at its end. Also, the chain of transforms from the image frame to the fixed frame (referred to herein as the "image frame transforms") includes the frame 610 to frame 1413 transform at its start and the frame 1412 to frame 1401 at its end. The inverse of the tool frame transforms would then start with the frame 1401 to frame 1402 transform and end with the frame 1403 to frame 618 transform.

Thus, if the unknown transform is the frame 1403 to frame 618 transform ($_e^n T$), it can be determined using transform equation (2) as follows:

$$_c^e T =\, _w^e T \cdot\, _c^w T =\, _n^e T \cdot\, _w^n T \cdot\, _c^w T \tag{3}$$

$$_n^e T =\, _c^e T \cdot\, _w^c T \cdot\, _n^w T \tag{4}$$

Such a solution can be used to estimate the position and orientation of the end effector as required in reference to FIG. 11 for cannulas of different curvatures and lengths.

On the other hand, if the unknown transform is the frame 1413 to frame 610 transform (it can be determined using transform equation (2) as follows:

$$_c^e T =\, _w^e T \cdot\, _c^w T =\, _w^e T \cdot\, _k^w T \cdot\, _c^k T \tag{5}$$

$$_k^c T =\, _e^c T \cdot\, _w^e T \cdot\, _k^w T \tag{6}$$

Such a solution can be used to estimate the position and orientation of the camera as required in reference to FIG. 12 for the tethered camera.

Still further, if the unknown transform is the frame 1402 to the fixed frame transform ($_{1402}^w T$), it can be determined using equation (2) as follows:

$$_c^e T =\, _w^e T \cdot\, _c^w T =\, _{1402}^e T \cdot\, _w^{1402} T \cdot\, _c^w T \tag{7}$$

$$_{1402}^w T =\, _c^w T \cdot\, _e^c T \cdot\, _{1402}^e T \tag{8}$$

Such a solution can be used to estimate the position and/or relative orientation of one movable structure relative to another movable structure as required in reference to FIG. 13 for the two movable structures 1302, 1311 where the frame of one of the movable structures is chosen as the fixed frame. Although both structures 1302, 1311 are assumed movable, the solution is also applicable where one of the structures 1302, 1311 is fixed in position (such as with a ceiling mounted robotic arm) to define the fixed reference frame while the other one of the structures 1302, 1311 is movable (such as on a patient side cart).

The above examples assume that $_c^e T$ is first determined by the processor so that it may perform computations in equations (3) through (8). As an alternative approach, a point in the tool frame ep may be associated with a point in the image cp by the following transformation:

$$_c^e T = \begin{bmatrix} R & T \\ 0, 0, 0 & 1 \end{bmatrix} \tag{9}$$

where R is a 3×3 rotation matrix and T is a 3D translation vector, so that:

$$^e p =\, _c^e T \cdot\, ^c p \tag{10}$$

Thus, by substituting the right side of equation (2) for $_c^e T$ in equation (10), points in the image frame may be directly mapped into points in the tool frame without first determining $_c^e T$. As an example of applying this alternative approach to performing block 1506, equation (10) may be rewritten in general form as follows:

$$ep =\, _n^e T \cdot\, _{(n-1)}^n T \cdot\, _{(k-1)}^{(n-1)} T \cdot\, _k^{(k-1)} T \cdot\, _c^k T \cdot cp \tag{11}$$

Now, as an example, if the transform $_k^{(k-1)} T$ is the unknown transform and its values are not time varying, then equation (11) may be rewritten as follows:

$$_{(k-1)}^k T \cdot \underbrace{_w^{(k-1)} T \cdot\, _{(n-1)}^w T \cdot\, _n^{(n-1)} T \cdot\, _e^n T \cdot\, ^e p}_{^{(k-1)} p} =\, \underbrace{_c^k T \cdot\, ^c p}_{^k p} \tag{12}$$

In this form, the unknown transform $_{(k-1)}^k T$ (and consequently, its inverse transform $_k^{(k-1)} T$) can be solved by a set of point pairs $\{^{(k-1)} p_i,\, ^k p_i\}$ where i=1 ... m. The point pairs can be derived from a single time instant or from a number of time instants. As examples of methods for solving equation (12), see, e.g., A. Lorusso, D. W. Eggert, and R. B. Fisher "A Comparison of Four Algorithms for Estimating 3-D Rigid Transformations," Proceedings BMVC, 1995.

If some knowledge of the transform $_{(k-1)}^k T$ is known (e.g., the number of independent parameters in the transform is fewer than 6), the transform can be rewritten as:

$$^k p = f(\Theta,\, ^{(k-1)} p) \tag{13}$$

where $\Theta = \{\theta_1, \ldots \theta_a\}$ are the free parameters. In this case, $\Theta$ in the most general form, can be solved by minimizing the following cost function using a standard non-linear optimization routine (e.g., Gauss-Newton method):

$$\Theta^* = \mathrm{argmin}_\Theta \Sigma_{i=1}^m \|^k p_i - f(\Theta;\, ^{(k-1)} p_i)\|^2 \tag{14}$$

Note that equation (14) applies to 3D points. For 2D points as applicable to equation (1), the parameters of the unknown transform may be solved by optimizing the following cost function:

$$\Theta^* = \mathrm{argmin}_\Theta \Sigma_{i=1}^m \|u_i - u''_i\|^2 \tag{15}$$

where $u'_i = [u'_i, v'_i]$ are the image coordinates of a point and $u_i = [u_i, v_i]^t$ is the image projection of the 3D point $^c p_i = [^c x_i,\, ^c y_i,\, ^c z_i]^T$.

If the camera parameters are unknown, the parameters can be estimated together with the unknown transform to be solved. If the lens is not perfect and has distortion (e.g., radial, tangential), the distortion parameters of the lens can also be estimated in a similar fashion as the camera intrinsic parameters (not shown here). For example, equation (15) may be modified as follows:

$$\{\Theta, f_x, f_y, u_0, v_0\}^* = \mathrm{argmin}_{\{\Theta, f_x, f_y, u_0, v_0\}} \Sigma_{i=1}^m \|u_i - u'_i\|^2 \tag{16}$$

As can be appreciated from the above examples, determining one unknown transform among the image and tool frame transforms is straightforward when all other transforms are known. When unknown parameters from more than one transform needs to be estimated, the parameters can be estimated by optimization similar to equations (14), (15) and (16).

In addition to solving an unknown transform by a set of point correspondences, filtering can be used for fitting the transform or the optimization. A filter from the Kalman filter family can be used. In particular, extended Kalman filters and unscented Kalman filters can be used for non-linear systems. An iterated extended information filter applicable for such use is described, for example, in U.S. patent application Ser. No. 12/495,304 (filed Jun. 30, 2009; entitled "Efficient Vision and Kinematic Data Fusion for Robotic Surgical Instruments and Other Applications"), which is incorporated herein by this reference. Benefits of using a filter include temporal smoothness and computational efficiency.

Even if a filter is not used, temporal smoothing on the estimated parameters over time can avoid abrupt change. In 1507, the processor optionally may perform temporal smoothing of the estimated unknown transform rather than immediately applying it to update the master-tool frame transform. Such smoothing would avoid abrupt changes in the control of the tool by its associated master control device. One method of performing such smoothing is to maintain a running average of estimated values for the unknown transform as the processor continually loops through the method by performing 1502-1508.

In 1508, the processor updates the master-tool frame transform using the filtered version of the estimated unknown transform and command movement of the tool in response to movement of the master control device using the updated master-tool transform. For example, a modified tool frame to camera frame transform using the filtered version of the estimated unknown transform may be determined. Then the master frame to eye frame transform may be modified so that the position and orientation of the tool frame 618 relative to the camera frame 610 are aligned with the position and orientation of the master frame 622 relative to the eye frame 612. After performing 1508, the processor then jumps back to 1502 to process the next vision measurement cycle.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system comprising:
   a control device;
   a manipulator configured to support a tool having a tool frame; and
   at least one processor coupled to the control device and the manipulator, the at least one processor configured to perform a method comprising:
      receiving one or more images captured by an image-capturing system, the image-capturing system having an image frame, wherein the tool is visible in the one or more images;
      determining, based on information in the one or more images, an estimated frame transform relating the image frame and the tool frame,
      wherein the estimated frame transform is used in defining an unknown frame transform between the image frame and the tool frame;
      determining, based on the estimated frame transform, an output movement for the tool in response to an input at the control device; and
      causing movement of the tool according to the output movement.

2. The system of claim 1, wherein determining the estimated frame transform comprises:
   determining an image-to-tool frame relationship between the image frame and the tool frame based on the information in the one or more images; and
   computing the estimated frame transform based on the image-to-tool frame relationship.

3. The system of claim 2, wherein determining the image-to-tool frame relationship comprises:
   identifying pose-indicating points of the tool in the one or more images; and
   determining the image-to-tool frame relationship using the pose-indicating points.

4. The system of claim 2,
   wherein the image-capturing system comprises a stereo camera and determining the image-to-tool frame relationship comprises determining 3D depth using a stereo triangulation; or
   wherein the image-capturing system comprises a monocular camera and determining the image-to-tool frame relationship comprises determining a 3D pose of the tool using a 2D to 3D recovery based on a geometry of the tool.

5. The system of claim 2, wherein determining the image-to-tool frame relationship comprises:
   determining point pairs derived from a single time instant.

6. The system of claim 2, wherein determining the image-to-tool frame relationship comprises:
   determining point pairs derived from a number of time instants.

7. The system of claim 1, wherein the method further comprises:
   specifying a sequence of frames from the image frame to the tool frame, the sequence of frames including the image frame, the tool frame, and one or more additional frames between the image frame and the tool frame; and
   specifying a plurality of frame transforms, each frame transform of the plurality of frame transforms corresponding to a pair of frames of the sequence of frames, the plurality of frame transforms including the unknown frame transform.

8. The system of claim 7,
   wherein at least one parameter of the unknown frame transform is known, and
   wherein determining the estimated frame transform comprises estimating an unknown parameter of the unknown frame transform.

9. The system of claim 7,
   wherein the plurality of frame transforms further comprises one or more known frame transforms, and
   wherein determining the output movement for the tool in response to the input at the control device comprises:
      using the one or more known frame transforms in addition to the estimated frame transform.

10. The system of claim 7, further comprising:
    a display that is viewable by an operator;
    wherein the control device has a control device frame and an eye frame is defined relative to the operator;
    wherein the display is configured to display information of images captured by the image-capturing system; and
    wherein determining the output movement for the tool in response to the input at the control device comprises:
       determining a master-to-tool transform by: using the estimated frame transform and one or more known frame transforms of the plurality of frame transforms, and aligning a master-to-eye transform with a tool-to-image transform, wherein the master-to-eye transform transforms points in the control device frame to corresponding points in the eye frame, and wherein the tool-to-image transform transforming points in the tool frame to corresponding points in the image frame, and using the master-to-tool transform to determine the output movement in response to the input.

11. The system of claim 7, wherein the sequence of frames comprises:
a sequence of frames from the image frame to a fixed frame; and
a second sequence of frames from the fixed frame to the tool frame.

12. The system of claim 7,
wherein the plurality of frame transforms comprises a second unknown frame transform, and
wherein the method further comprises: determining a second estimated frame transform for the second unknown frame transform, using the estimated frame transform and one or more known frame transforms of the plurality of frame transforms, and
wherein determining the output movement for the tool in response to the input at the control device comprises: using the second estimated frame transform in addition to the estimated frame transform.

13. A method for operating a system comprising a control device and a manipulator configured to support a tool having a tool frame, the method comprising:
receiving one or more images captured by an image-capturing system, the image-capturing system having an image frame, wherein the tool is visible in the one or more images;
determining, based on information in the one or more images, an estimated frame transform relating the image frame and the tool framem
wherein the estimated frame transform is used in defining an unknown frame transform between the image frame and the tool frame;
determining, based on the estimated frame transform, an output movement for the tool in response to an input at the control device; and
causing movement of the tool according to the output movement.

14. The method of claim 13, wherein determining the estimated frame transform comprises:
determining an image-to-tool frame relationship between the image frame and the tool frame based on the information in the one or more images; and
computing the estimated frame transform based on the image-to-tool frame relationship.

15. The method of claim 14, wherein determining the image-to-tool frame relationship comprises:
identifying pose-indicating points of the tool in the one or more images; and
determining the image-to-tool frame relationship using the pose-indicating points.

16. The method of claim 13, further comprising:
specifying a sequence of frames from the image frame to the tool frame, the sequence of frames including the image frame, the tool frame, and one or more additional frames between the image frame and the tool frame; and
specifying a plurality of frame transforms, each frame transform of the plurality of frame transforms corresponding to a pair of frames of the sequence of frames, the plurality of frame transforms including the unknown frame transform.

17. The method of claim 16,
wherein at least one parameter of the unknown frame transform is known, and
wherein determining the estimated frame transform comprises estimating an unknown parameter of the unknown frame transform.

18. The method of claim 13, wherein the control device has a control device frame, wherein the system further comprises a display that is viewable by an operator, wherein an eye frame is defined relative to the operator, and wherein determining the output movement for the tool in response to the input at the control device comprises:
determining a master-to-tool transform by: using the estimated frame transform and one or more known frame transforms, and aligning a master-to-eye transform with a tool-to-image transform, wherein the master-to-eye transform transforms points in the control device frame to corresponding points in an eye frame, and wherein the tool-to-image transform transforming points in the tool frame to corresponding points in the image frame, and
using the master-to-tool transform to determine the output movement in response to the input.

19. A non-transitory machine-readable medium comprising a plurality of machine-readable instructions executed by one or more processors associated with a system, the system comprising a control device and a manipulator configured to support a tool having a tool frame, and the plurality of machine-readable instructions causing the one or more processors to perform a method comprising:
receiving one or more images captured by an image-capturing system, the image-capturing system having an image frame, wherein the tool is visible in the one or more images;
determining, based on information in the one or more images, an estimated frame transform relating the image frame and the tool frame,
wherein the estimated frame transform is used in defining an unknown frame transform between the image frame and the tool frame;
determining, based on the estimated frame transform, an output movement for the tool in response to an input at the control device; and
causing movement of the tool according to the output movement.

20. The non-transitory machine-readable medium of claim 19, wherein determining the estimated frame transform comprises:
determining an image-to-tool frame relationship between the image frame and the tool frame based on the information in the one or more images, and
computing the estimated frame transform based on the image-to-tool frame relationship; and wherein
the method further comprises:
specifying a sequence of frames from the image frame to the tool frame, the sequence of frames including the image frame, the tool frame, and one or more additional frames between the image frame and the tool frame; and
specifying a plurality of frame transforms, each frame transform of the plurality of frame transforms corresponding to a pair of frames of the sequence of frames, the plurality of frame transforms including the unknown frame transform.

* * * * *

UNITED STATES PATENT AND TRADEMARK OFFICE
CERTIFICATE OF CORRECTION

PATENT NO. : 11,284,952 B2
APPLICATION NO. : 16/779564
DATED : March 29, 2022
INVENTOR(S) : Zhao et al.

It is certified that error appears in the above-identified patent and that said Letters Patent is hereby corrected as shown below:

In the Claims

Claim 13, at Column 23, Line number 34, the word "framem" should read -- frame --.

Signed and Sealed this
Seventeenth Day of May, 2022

Katherine Kelly Vidal
*Director of the United States Patent and Trademark Office*